(12) United States Patent
Seo et al.

(10) Patent No.: US 12,291,583 B2
(45) Date of Patent: May 6, 2025

(54) CARRAGEENAN DERIVATIVE, PROBE FOR LABELLING MACROPHAGES, AND METHOD FOR PREPARING SAME

(71) Applicants: KOREA UNIVERSITY RESEARCH AND BUSINESS FOUNDATION, Seoul (KR); SEOUL NATIONAL UNIVERSITY R&DB FOUNDATION, Seoul (KR)

(72) Inventors: Hong Seog Seo, Seoul (KR); Yong Jik Lee, Incheon (KR); Jae Min Jeong, Seoul (KR); Yun Sang Lee, Gyeonggi-do (KR); Ji Yong Park, Incheon (KR)

(73) Assignees: KOREA UNIVERSITY RESEARCH AND BUSINESS FOUNDATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 796 days.

(21) Appl. No.: 17/439,177

(22) PCT Filed: Mar. 13, 2020

(86) PCT No.: PCT/KR2020/003550
§ 371 (c)(1),
(2) Date: Sep. 14, 2021

(87) PCT Pub. No.: WO2020/185042
PCT Pub. Date: Sep. 17, 2020

(65) Prior Publication Data
US 2022/0162347 A1    May 26, 2022

(30) Foreign Application Priority Data

Mar. 14, 2019   (KR) .................. 10-2019-0029255
Mar. 13, 2020   (KR) .................. 10-2020-0031088

(51) Int. Cl.
*C08B 37/00*   (2006.01)
*G01N 33/58*   (2006.01)

(52) U.S. Cl.
CPC ............. *C08B 37/00* (2013.01); *G01N 33/58* (2013.01)

(58) Field of Classification Search
None
See application file for complete search history.

(56) References Cited

U.S. PATENT DOCUMENTS

2017/0189549 A1   7/2017   Helin

FOREIGN PATENT DOCUMENTS

| CN | 106498066 | 3/2017 |
| KR | 101771697 | 8/2017 |

OTHER PUBLICATIONS

Perrone, M., et al., "Natural dendrimers: Synthesis and in vitro characterization of glycogen-cysteamine conjugates," European Journal of Pharmaceutics and Biopharmaceutics 115 (2017) 168-176.
Rahmat, D., et al., "Design and synthesis of a novel cationic thiolated polymer," International Journal of Pharmaceutics 411 (2011) 10-17.
Moghadam, A., et al., "Non-ionic thiolated cyclodextrins—the next generation," International Journal of Nanomedicine 2018:13 4003-4013.
Guan, J., et al., "Applications of Carrageenan in Advanced Drug Delivery," Seaweed Polysaccharides, 2017, Chapter 15, pp. 283-303.

*Primary Examiner* — Layla D Berry
(74) *Attorney, Agent, or Firm* — DUANE MORRIS LLP; Gregory M. Lefkowitz; Brandon A. Chan

(57) ABSTRACT

A carrageenan derivative according to the present disclosure can quickly and easily detect and label the presence of inflammation-related macrophages and, particularly, can accurately and easily identify M1-type macrophages highly associated with early inflammation. In addition, the carrageenan derivative has advantages in that it can be produced easily, environmental pollution is minimized because a small amount of organic solvent is used, and initial cost is low.

17 Claims, 15 Drawing Sheets

FIG. 4

COMPOUND SUMMARY

[5-[4,5-Dihydroxy-6-(hydroxymethyl)-3-sulfonatooxyoxan-2-yl]oxy-2,4-dihydroxy-6-(sulfonatooxymethyl)oxan-3-yl] sulfate

| | |
|---|---|
| PubChem CID: | 91972149 |
| Structure: | (2D structure) Find Similar Structures |
| Molecular Formula: | $C_{12}H_{19}O_{20}S_3{}^{-3}$ |
| Chemical Names: | 9064-57-7<br>CARRAGEENAN LAMBDA |
| Molecular Weight: | 579.5 g/mol |
| Dates: | Modify: 2019-08-17   Create: 2015-11-02 |

Unit

MALDI-TOF

— Lamda-Carrageenan

—— STEP1_Cysteamine conjugated compound

······ STEP2_RITC conjugated compound

CARRAGEENAN DERIVATIVE, PROBE FOR LABELLING MACROPHAGES, AND METHOD FOR PREPARING SAME

CROSS-REFERENCE TO RELATED APPLICATIONS

This application is a § 371 national stage entry of International Application No. PCT/KR2020/003550, filed on Mar. 13, 2020, which claims priority to Korean Patent Application No. 10-2019-0029255, filed on Mar. 14, 2019, and Korean Patent Application No. 10-2020-0031088, field Mar. 13, 2020, the entire contents of which are incorporated herein by reference.

TECHNICAL FIELD

The present disclosure relates to a probe for labeling macrophages, which is capable of specifically labeling macrophages induced by inflammation. More particularly, the present disclosure relates to a carrageenan derivative which allows the detection of the presence of macrophages by interacting with CD80 existing specifically on the surface of macrophages, a probe for labeling macrophages in the form of a complex bound with a radioisotope or a fluorescent dye, a method for preparing the same, a method for providing information about the location of macrophages, and a kit for labeling macrophages including the same.

BACKGROUND ART

Inflammation is a part of biological response of body tissues to harmful stimuli, such as pathogens, damaged cells or irritants, and is a protective response involving immune cells, blood vessels and molecular mediators. The function of inflammation is to eliminate the initial cause of cell injury, clear out necrotic cells and damaged tissues at the wound site and regenerate tissues.

Therefore, development of an imaging technology capable of tracing the movement of inflammatory cells noninvasively can be a foundation for various inflammatory cell-related researches. Although experiments are being conducted on treatment of various diseases induced by inflammatory cells in various animal models, there is a difficulty in that the expensive animal models have to be sacrificed repeatedly because an imaging probe capable of evaluating therapeutic effect quantitatively and effectively has not been developed.

There are high hopes for several radiopharmaceuticals since they allow the evaluation of the effect of cell therapy through noninvasive nuclear medical imaging and are clinically applicable.

Especially, various imaging probe materials capable of effectively labeling macrophages have been developed since they allow real-time monitoring of macrophages involved in various diseases through noninvasive imaging and can be applied widely to monitoring of the onset, progression and treatment of various diseases such as inflammation, arteriosclerosis, autoimmune disease, tumor, etc.

As a representative example, a method of labeling macrophages using fluorine-18 fluorodeoxyglucose ($^{18}$F-FDG) has been reported. This method uses the metabolic characteristics of macrophages. Specifically, since macrophages exhibit increased glucose uptake as well as increased uptake of FDG, which is a glucose derivative, as compared to other cells, presence of macrophages can be detected using these characteristics. However, the technique of labeling and imaging macrophages using $^{18}$F-FDG have some limitations in that it is based on the metabolic characteristics of macrophages. First, because FDG is a glucose analog, it is affected by glucose and metabolism-related hormones in blood and, therefore, the accuracy and reproducibility of macrophage labeling may vary significantly depending on physical condition. In addition, the physical condition should be maintained constant prior to diagnosis. Furthermore, it is limited in use in high-risk groups because the conditions such as fasting, blood sugar, etc. should be satisfied. Second, since the brain and heart use blood glucose as nutrients, the foci occurring in the brain and heart cannot be detected. Finally, selective detection of presence of proinflammatory M1 macrophages is impossible with FDG.

Accordingly, development of a new method capable of detecting phagocytosis, particularly by macrophages, without being affected by physical condition is necessary.

DISCLOSURE

Technical Problem

The present disclosure is directed to providing a carrageenan derivative with a modified structure, which can bind specifically to CD80 of macrophages.

The present disclosure is also directed to providing a probe for labeling macrophages, wherein a fluorescent dye or a radioisotope and the carrageenan derivative are bound.

The present disclosure is also directed to providing a method for preparing the carrageenan derivative and the probe for labeling macrophages easily and conveniently in large scales.

The present disclosure is also directed to providing a method for providing information about the location of macrophages.

Technical Solution

The present disclosure provides a carrageenan derivative formed as a hydroxy group of a galactose or 3,6-anhydrogalactose moiety of carrageenan having a repeat unit represented by Chemical Formula 1 is oxidized to an aldehyde group through periodate oxidation, and the aldehyde group is substituted with a compound represented by Chemical Formula 2 or Chemical Formula 3 and then reduced.

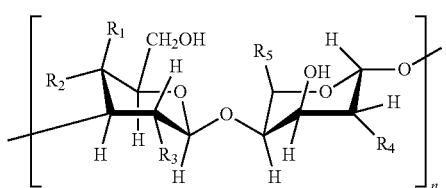

[Chemical Formula 1]

[Chemical Formula 2]

-continued

[Chemical Formula 3]

In the above chemical formulas, each of $R_1$ to $R_5$, which are identical to or different from each other, is any one selected from a group consisting of —H, —OH, —CH$_3$, —CH$_2$OH, —COOH or —OSO$_3^-$, n is an integer from 1 to 10,000, and o is an integer from 1 to 10.

The carrageenan represented by Chemical Formula 1 may be any one represented by those selected from Chemical Formula a to Chemical Formula c, specifically λ-carrageenan represented by Chemical Formula c.

[Chemical Formula a]

α-carrageenan

[Chemical Formula b]

β-carrageenan

[Chemical Formula c]

λ-carrageenan

In the above chemical formulas, n may be an integer from 50 to 10,000.

The carrageenan derivative may act as a ligand of CD80 of macrophages.

The macrophages may be M1-type macrophages.

The carrageenan derivative may have one or two compound represented by Chemical Formula 2 or Chemical Formula 3 per molecule bound as affinity groups.

The carrageenan derivative may have a degree of substitution of 1-40 mol %.

The present disclosure also provides a method for preparing a carrageenan derivative, which includes:

1) a step of preparing carrageenan-aldehyde having repeat units represented by Chemical Formulas 1 and 4 by reacting carrageenan having a repeat unit represented by Chemical Formula 1 with an oxidizing agent;

2) a step of substituting the aldehyde group of the carrageenan-aldehyde with a compound of Chemical Formula 2 or Chemical Formula 3 by reacting the carrageenan-aldehyde prepared in the step 1) with a compound represented by Chemical Formula 2 or Chemical Formula 3; and 3) a step of reacting the substituted carrageenan derivative prepared in the step 2) with a reducing agent.

[Chemical Formula 1]

[Chemical Formula 2]

[Chemical Formula 3]

[Chemical Formula 4]

In the above chemical formulas, each of $R_1$ to $R_5$ is independently any one selected from a group consisting of —H, —OH, —CH$_3$, —CH$_2$OH, —COOH and —OSO$_3^-$, each of n and m is an integer from 1 to 10,000, and o is an integer from 1 to 10.

The oxidizing agent may be sodium periodate.

The oxidizing agent may be added with an amount of 1-10 molar equivalents per unit of the carrageenan having a repeat unit represented by Chemical Formula 1.

The step 1) may be performed at 10-30° C. for 1-180 minutes.

In the step 2), the reaction may be carried out such that 1-10, specifically 2-6, molecules of the compound represented by Chemical Formula 2 or Chemical Formula 3 is reacted per molecule of the carrageenan-aldehyde.

In the step 3), 1-100 molar equivalents of the reducing agent may be added per unit of the carrageenan having a repeat unit represented by Chemical Formula 1.

The step 3) may be performed at −10 to 10° C. for 1-240 minutes.

The reducing agent may be sodium cyanoborohydride (NaCNBH$_3$) or sodium borohydride.

The present disclosure also provides a probe for labeling macrophages wherein a fluorescent dye or a radioisotope and the carrageenan derivative described above are bound.

The fluorescent dye may be one or more selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA and biotin.

The radioisotope may be one or more selected from a group consisting of C-11, F-18, Ga-67, Ga-68, Cu-64, I-123, I-124, I-125, Zr-89, In-111, Tc-99m, Y-90, Re-186, Re-188, Lu-177, Ac-225, At-211 and 1-131.

The macrophages may be derived by an inflammation-inducing factor.

The probe for labeling macrophages may specifically label M1-type macrophages.

The present disclosure also provides a kit for imaging macrophages, which includes the probe for labeling macrophages.

The present disclosure also provides a method for preparing a probe for labeling macrophages, which includes:

a) a step of preparing carrageenan-aldehyde having repeat units represented by Chemical Formulas 1 and 4 by reacting carrageenan having a repeat unit represented by Chemical Formula 1 with an oxidizing agent;

b) a step of substituting an aldehyde group of the carrageenan-aldehyde with a compound of Chemical Formula 2 by reacting the carrageenan-aldehyde prepared in the step a) with a compound represented by Chemical Formula 2 or Chemical Formula 3;

c) a step of reacting the substituted carrageenan derivative prepared in the step b) with a reducing agent; and d) a step of reacting the carrageenan derivative prepared in the step c) with a radioisotope or an isothiocyanate-modified fluorescent dye.

—COOH and —OSO$_3^-$, each of n and m is an integer from 1 to 10,000, and o is an integer from 1 to 10.

The present disclosure also provides a method for preparing a probe for labeling macrophages, which includes:

i) a step of preparing carrageenan-aldehyde having repeat units represented by Chemical Formulas 1 and 4 by reacting carrageenan having a repeat unit represented by Chemical Formula 1 with an oxidizing agent;

ii) a step of substituting an aldehyde group of the carrageenan-aldehyde with a compound of Chemical Formula 3 by reacting the carrageenan-aldehyde prepared in the step i) with a compound represented by Chemical Formula 2 or Chemical Formula 3;

iii) a step of reacting the substituted carrageenan derivative prepared in the step ii) with a reducing agent; and iv) a step of conducting copper-free click reaction of the carrageenan derivative prepared in the step iii) with an azide compound represented by Chemical Formula 5:

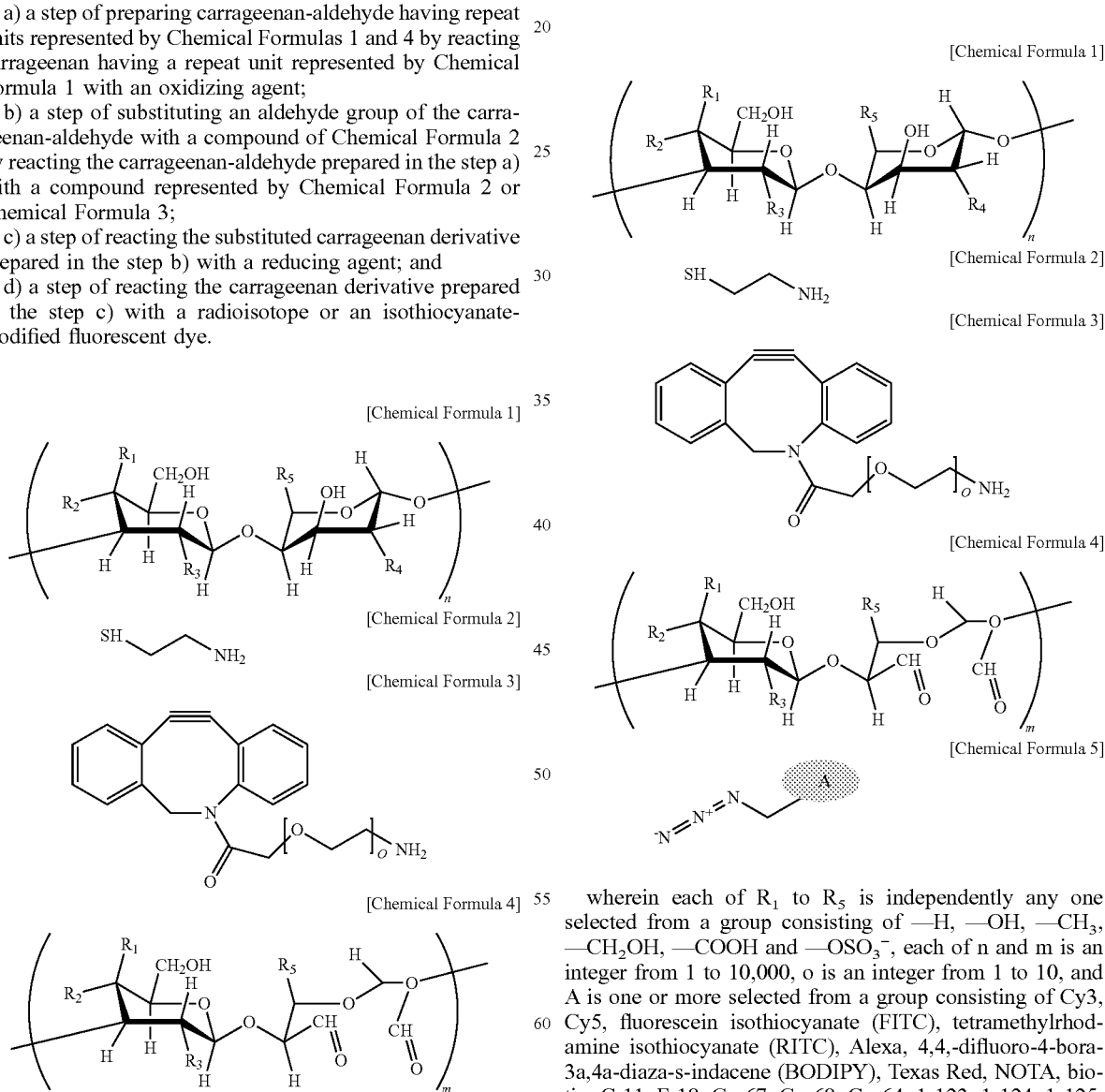

In the above chemical formulas, each of $R_1$ to $R_5$ is independently any one selected from a group consisting of —H, —OH, —CH$_3$, —CH$_2$OH, —COOH and —OSO$_3^-$, each of n and m is an integer from 1 to 10,000, o is an integer from 1 to 10, and A is one or more selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA, biotin, C-11, F-18, Ga-67, Ga-68, Cu-64, 1-123, 1-124, 1-125, Zr-89, In-111, Tc-99m, Y-90, Re-186, Re-188, Lu-177, Ac-225, At-211 and 1-131.

The present disclosure also provides a method for providing information about the location of macrophages by administering a composition containing the probe for labeling macrophages to an isolated biological sample.

The macrophages may be inflammation-related M1-type macrophages.

Advantageous Effects

A carrageenan derivative according to the present disclosure can quickly and easily detect and label the presence of inflammation-related macrophages and, particularly, can accurately and easily identify M1-type macrophages highly associated with early inflammation.

In addition, the carrageenan derivative has advantages in that it can be produced easily, environmental pollution is minimized because a small amount of organic solvent is used, and initial cost is low.

Furthermore, the carrageenan derivative is advantageous in that it is not necessary to maintain physical condition prior to diagnosis since it interacts directly with CD80, which is cell surface receptor of macrophages, without being affected by metabolism, unlike the existing materials for labeling inflammation-related cells.

BRIEF DESCRIPTION OF DRAWINGS

FIG. 4 shows the average molecular weight of carrageenan (A-carrageenan).

BEST MODE

Figure 1A:
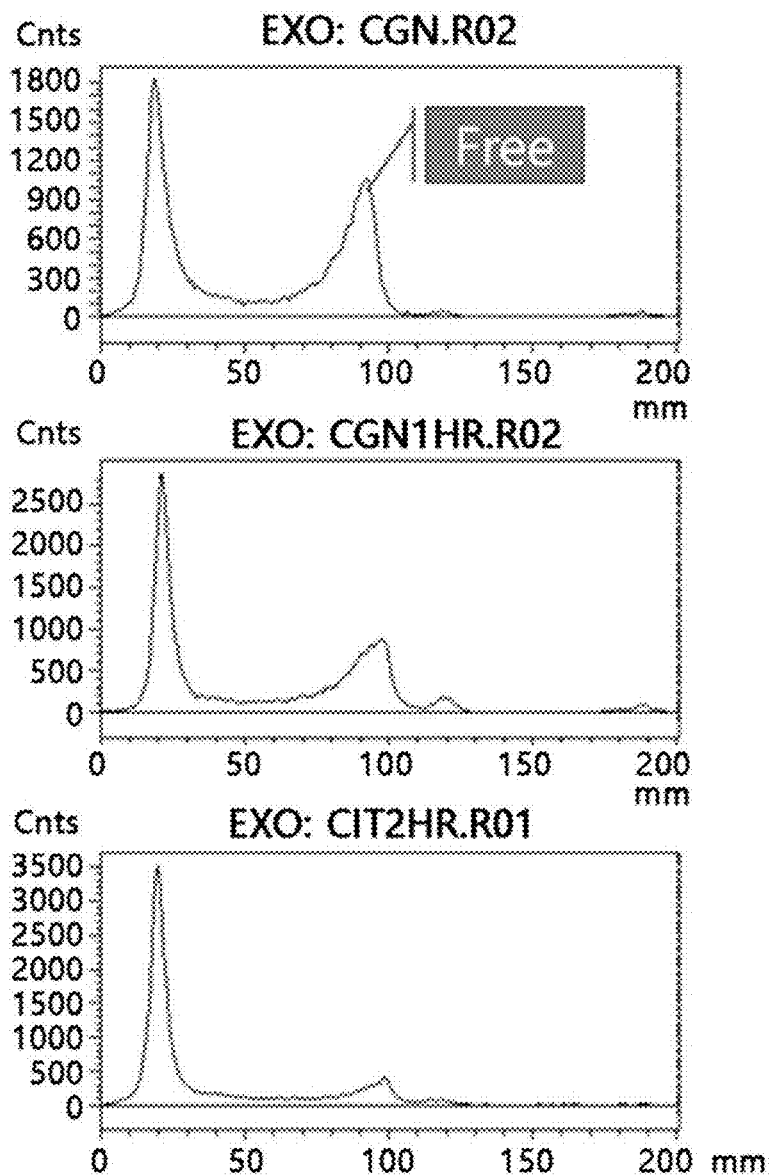
FIG. 1A shows an instant thin layer chromatography (iTLC) measurement result in citric acid, FIG. 1B in saline, and FIG. 1C in acetone.

The present disclosure relates to a carrageenan derivative acting as a ligand of CD80, which is one of the cell membrane receptors of macrophages, particularly M1-type macrophages. It is synthesized from carrageenan having a repeat unit represented by Chemical Formula 1 and can label macrophages quickly, accurately and repeatedly. When the isotope $^{99m}$Tc or RITC is attached, it can specifically image inflammation-related macrophages, particularly M1-type macrophages.

Unlike the existing 18F-FDG label, the carrageenan derivative of the present disclosure exhibits an effect by directly binding to CD80, which is one of the cell membrane receptors of macrophages. The inventors of the present disclosure have developed a probe for labeling macrophages and a method for preparing the same using these characteristics. It has been confirmed that the probe for labeling macrophages can image the presence of M1-type macrophages, which are proinflammatory macrophages, molecular biologically.

Hereinafter, various aspects and exemplary embodiments of the present disclosure will be described more specifically.

An aspect of the present disclosure relates to a carrageenan derivative formed as a hydroxy group of a galactose or 3,6-anhydrogalactose moiety of carrageenan having a repeat unit represented by Chemical Formula 1 is oxidized to an aldehyde group through periodate oxidation, and the aldehyde group is substituted with a compound represented by Chemical Formula 2 or Chemical Formula 3 and then reduced.

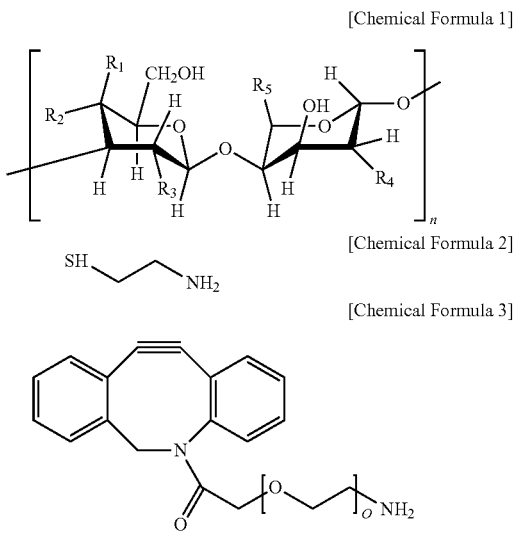

In the above chemical formulas, each of $R_1$ to $R_5$, which are identical to or different from each other, is any one selected from a group consisting of —H, —OH, —CH$_3$, —CH$_2$OH, —COOH or —OSO$_3^-$, n is an integer from 1 to 10,000, and o is an integer from 1 to 10.

Unless specified otherwise, the carrageenan represented by Chemical Formula 1 of the present disclosure is not limited particularly. For optimization of the carrageenan derivative for specific binding to macrophages, the carrageenan may be one having a molecular weight of specifically 10,000-3,000,000 Da, more specifically 10,000-1,000,000 Da.

The term "carrageenan" used in the present disclosure refers to a polymer having a repeat unit represented by Chemical Formula 1, and may be used to include the salt forms of carrageenan. Specifically, the carrageenan may be any one selected from those represented by Chemical Formula a to Chemical Formula c.

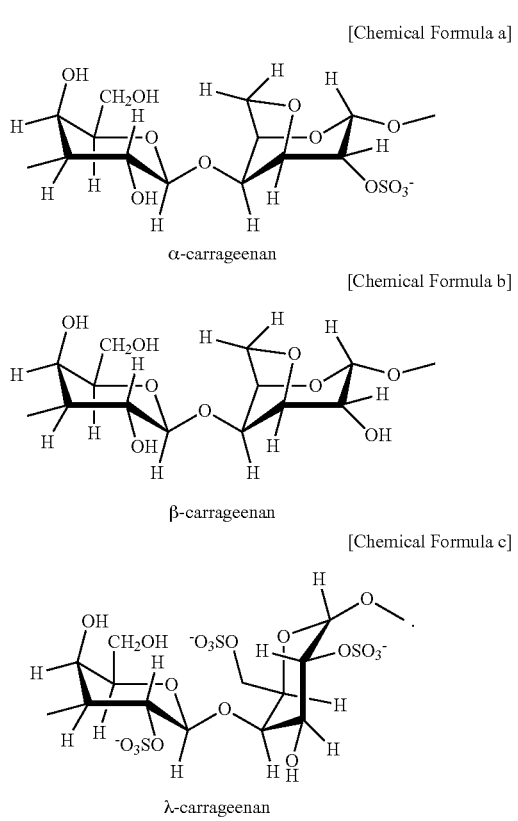

In the above chemical formulas, m may be an integer from 50 to 10,000.

In the present disclosure, the periodate oxidation means a reaction whereby oxidation and breakage of carbon-carbon bond occur at the same time from reaction with periodate ($NaIO_4$) when two hydroxyl groups are adjacent to each other, one hydroxyl group is adjacent to an aldehyde or a ketone, or a hemiacetal and a hemiketal in dynamic equilibrium with an aldehyde or a ketone are present.

In general, when a polysaccharide such as carrageenan is oxidized by an oxidizing agent, etc., the hydroxy group at 2-, 3- or both positions of the polysaccharide is changed into an aldehyde group as an aliphatic ring structure such as galactose or 3,6-anhydrogalactose is opened (ring opening). A carrageenan derivative substituted with the compound represented by Chemical Formula 2 or Chemical Formula 3 is formed as the aldehyde group of the polysaccharide reacts with the amine group of the compound represented by Chemical Formula 2 or Chemical Formula 3 through imine bonding. Subsequently, the carrageenan derivative of the present disclosure may be obtained by reducing a double bond formed from the reaction of the amine group of the compound represented by Chemical Formula 2 or Chemical Formula 3 and the aldehyde group of carrageenan with a reducing agent.

In the present disclosure, the carrageenan oxidized through periodate oxidation is referred to as carrageenan-aldehyde. Specifically, the carrageenan-aldehyde may contain repeat units represented by Chemical Formula 1 and Chemical Formula 4.

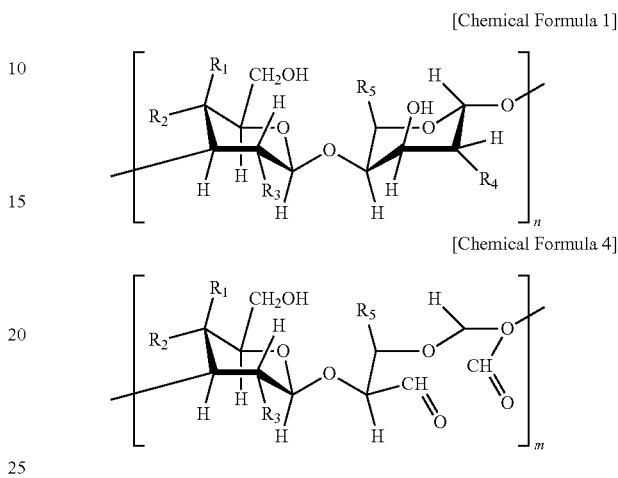

In the above chemical formulas, each of $R_1$ to $R_5$ is independently any one selected from a group consisting of —H, —OH, —$CH_3$, —$CH_2OH$, —COOH and —$OSO_3^-$, and each of n and m, which indicate the number of the repeat units, is an integer from 1 to 10,000.

The repeat units of the carrageenan-aldehyde may include 60-99 mol % of the repeat unit of Chemical Formula 1 and 1-40 mol % of the repeat unit of Chemical Formula 4, specifically 80-90 mol % of the repeat unit of Chemical Formula 1 and 10-25 mol % of the repeat unit of Chemical Formula 4.

The concept of the degree of substitution is used when substituting the aldehyde group of the carrageenan-aldehyde with the compound represented by Chemical Formula 2 or Chemical Formula 3 by reacting the carrageenan-aldehyde with the compound represented by Chemical Formula 2 or Chemical Formula 3. In the present disclosure, the term "degree of substitution" refers to the degree of modification/substitution with each of the compound represented by Chemical Formula 2 or Chemical Formula 3.

For the compound represented by Chemical Formula 2, a fluorescent dye modified with a functional group or a radioisotope may be bonded. The functional group may be a thiocyanate (—SCN) or isothiocyanate (—NCS) group. The fluorescent dye may be one or more selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA and biotin.

And, for the compound represented by Chemical Formula 3, a fluorescent dye or a radioisotope may be bonded through copper-free click chemistry. The fluorescent dye or radioisotope may be introduced from a compound represented by Chemical Formula 5 (azide compound).

Since the carrageenan derivative effectively bind to the surface of inflammation-related cells by interacting specifically with CD80 existing on the surface of macrophages, particularly M1-type macrophages, it can be used to detect and diagnose the presence of inflammation.

In general, when an NHS, acrylate, thiol or maleimide group is introduced to the surface of a derivative, interaction is formed regardless of cell type through covalent bonding with the amine or thiol group of proteins existing on the cell surface. However, in the present disclosure, a carrageenan derivative is synthesized by substituting and reducing carrageenan so that it can bind specifically to inflammation-related macrophages. Through this, interaction can be formed specifically with inflammation-related macrophages, particularly M1-type macrophages.

The carrageenan derivative is synthesized by the following process:

1) a step of preparing a carrageenan-aldehyde having repeat units represented by Chemical Formulas 1 and 4 by reacting carrageenan having a repeat unit represented by Chemical Formula 1 with an oxidizing agent;

2) a step of substituting an aldehyde group of the carrageenan-aldehyde with a compound of Chemical Formula 2 or 3 by reacting the carrageenan-aldehyde prepared in the step 1) with a compound represented by Chemical Formula 2 or 3; and 3) a step of reacting the substituted carrageenan derivative prepared in the step 2) with a reducing agent.

1) A carrageenan-aldehyde having repeat units represented by Chemical Formulas 1 and 4 is prepared by reacting carrageenan having a repeat unit represented by Chemical Formula 1 with an oxidizing agent.

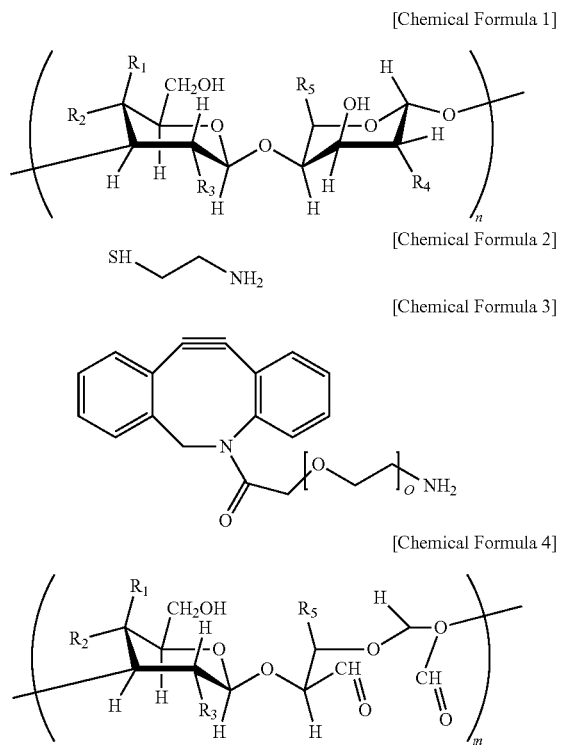

[Chemical Formula 1]

[Chemical Formula 2]

[Chemical Formula 3]

[Chemical Formula 4]

In the above chemical formulas, each of $R_1$ to $R_5$ is independently any one selected from a group consisting of —H, —OH, —CH$_3$, —CH$_2$OH, —COOH and —OSO$_3^-$, each of n and m is an integer from 1 to 10,000, and o is an integer from 1 to 10.

For prevention of aggregation, the concentration of the carrageenan having a repeat unit represented by Chemical Formula 1 may be specifically lower than 10 mg/mL, most specifically 1-5 mg/mL.

Through the step 1), the carrageenan having a repeat unit represented by Chemical Formula 1 is oxidized by an oxidizing agent and the hydroxy group at 2-, 3- or both positions of the carrageenan is changed into an aldehyde group as an aliphatic ring structure such as galactose or 3,6-anhydrogalactose is opened (ring opening). As a result, carrageenan-aldehyde having repeat units represented by Chemical Formulas 1 and 4 is prepared. Specifically, the degree of oxidation of the carrageenan-aldehyde defined as the molar ratio (%) of repeat units (Chemical Formula 4) having aldehyde groups formed as the ring structure of carrageenan is opened in all carrageenan repeat units may be represented by a value between 0 and 1 or between 0 mol % and 100 mol %. Specifically, the repeat units constituting the carrageenan-aldehyde after the step 1) may include 60-99 mol % of the repeat unit of Chemical Formula 1 and 1-40 mol % of the repeat unit of Chemical Formula 4, specifically 80-90 mol % of the repeat unit of Chemical Formula 1 and 10-25 mol % of the repeat unit of Chemical Formula 4.

When the mol % of the repeat units represented by Chemical Formula 1 and Chemical Formula 4 of the carrageenan-aldehyde satisfy the condition descried above, the anticipated macrophage targeting effect can be achieved since fluorescent dyes and radioisotopes enough for binding and sufficient interaction with CD80 in macrophages can be ensured.

Since carrageenan, which is a biocompatible, biodegradable polymer, can be safely applied to the human body and can specifically label macrophages, which are inflammation-related cells, by being conjugated with a fluorescent dye or a radioisotope by opening a ring structure with the backbone structure of carrageenan binding specifically to macrophages remaining intact, thereby maximizing the macrophage-specific delivery characteristics of carrageenan, it can be used variously for detection and diagnosis of early inflammation-related macrophages.

The oxidizing agent is not specially limited as long as it can break the ring structure of carrageenan. Specifically, sodium periodate (NaIO$_4$) may be used.

Specifically, the oxidizing agent may be added with an amount of 1-10 molar equivalents, more specifically 1-5 molar equivalents, per unit of the carrageenan having a repeat unit represented by Chemical Formula 1. Specifically, the oxidizing agent may be reacted for 1-180 minutes, more specifically for 10-60 minutes.

Specifically, in the present disclosure, the oxidizing agent may be added with an amount of at least 1-10 molar equivalents so that 90% or more of the carrageenan derivative is labeled with Tc-99m or a fluorescent dye.

After the reaction with the oxidizing agent, a purification step of dialyzing with distilled water may be further included.

Then, 2) an aldehyde group of the carrageenan-aldehyde is substituted with a compound of Chemical Formula 2 or Chemical Formula 3 by reacting the carrageenan-aldehyde prepared in the step 1) with a compound represented by Chemical Formula 2 or Chemical Formula 3.

Specifically, after dissolving the carrageenan-aldehyde prepared in the step 1) in distilled water, reaction is carried out by adding the compound represented by Chemical Formula 2 or Chemical Formula 3. For example, the aldehyde group of the carrageenan-aldehyde may be reacted with an amine group of the compound of Chemical Formula 2 or Chemical Formula 3 by adding the compound of Chemical Formula 2 or Chemical Formula 3. Since the compound of Chemical Formula 2 or Chemical Formula 3, e.g., cysteamine or DBCO, has an amine group, the compound of Chemical Formula 2 or Chemical Formula 3 used in the step 2) may be used in itself without a preparation process. In addition, since the carrageenan-aldehyde and the compound of Chemical Formula 2 or Chemical Formula 3 are water-soluble, the reaction may be carried out in an aqueous solution by dissolving in water.

Because the aldehyde group of the carrageenan-aldehyde is highly reactive, if it remains without reacting with the compound represented by Chemical Formula 2 or Chemical Formula 3, accuracy may be decreased when interacting with the CD80 of macrophages afterwards.

Accordingly, it is preferred that the compound represented by Chemical Formula 2 or Chemical Formula 3 is mixed with an excess amount. The amount of the compound represented by Chemical Formula 2 or Chemical Formula 3 may be selected adequately depending on the degree of oxidation of the carrageenan-aldehyde. Specifically, 1-100 molar equivalents of the aldehyde group of the carrageenan-aldehyde may be added, and the reaction may be performed for 10-240 minutes, specifically for 30-180 minutes.

If unreacted aldehyde group remains in the carrageenan-aldehyde after the step 2), a step of blocking the same may be further included. For the blocking, a substance that can react with a carboxyl group or an aldehyde group may be used without special limitation. Specifically, an amine may be used. More specifically, the amine may be a $C_{1-5}$ linear or branched alkyl carbazate or a $C_{1-5}$ lower alkanolamine.

Specifically, the step 2) may be performed in distilled water or a buffer solution. The buffer solution may have a pH of 5-7, more specifically a pH of 5-6.5.

One to ten, specifically two to six, molecules of the compound represented by Chemical Formula 2 or Chemical Formula 3 of the present disclosure may be reacted per molecule of a carrageenan aldehyde or carrageenan.

Subsequently, 3) a carrageenan derivative is prepared by reacting the substituted carrageenan derivative prepared in the step 2) with a reducing agent.

The substituted carrageenan derivative prepared in the step 2) may be reacted by adding a reducing agent. The reducing agent reduces a double bond formed from the reaction of the amine group the compound represented by Chemical Formula 2 or Chemical Formula 3 with the aldehyde group of the carrageenan-aldehyde.

The reducing agent may be selected adequately depending on the degree of substitution, which refers to the degree of modification/substitution with the compound represented by Chemical Formula 2 or Chemical Formula 3. Specifically, it may be added with an amount of 2-100 molar equivalents, more specifically 10-50 molar equivalents, of the compound represented by Chemical Formula 2 or Chemical Formula 3, and the reaction may be performed for 10-240 minutes, specifically for 30-180 minutes.

The reducing agent may be sodium cyanoborohydride ($NaCNBH_3$) or sodium borohydride.

Specifically, after the reaction with the reducing agent, a purification step of dialyzing with distilled water may be further included.

When preparing the carrageenan derivative, it is the most important that it is labeled with Tc-99m or a fluorescent dye. For labeling of at least 90%, in addition to the oxidizing agent, the concentrations of the compound of Chemical Formula 2 or 3 and the reducing agent are also important. Accordingly, it is recommended that the concentrations of the compound of Chemical Formula 2 or 3 and the reducing agent are within the above-described ranges. A probe for labeling macrophages may be obtained from a click chemical reaction of the carrageenan derivative prepared as described above. Specifically, 1 molar equivalent or more, most specifically 1-10 molar equivalents, of an azide compound represented by Chemical Formula 5 may be introduced based on 1 mol of the carrageenan derivative.

Another aspect of the present disclosure relates to a kit for imaging macrophages, which includes a fluorescent dye or a radioisotope; and a probe for labeling macrophages with the carrageenan derivative bound.

The probe for labeling macrophages according to the present disclosure overcomes the limitation of diagnosis of inflammation using 18F-FDG and informs whether inflammation is being aggravated or healed. First, because FDG is a glucose analog, it is affected by glucose and metabolism-related hormones in blood. Therefore, fasting is necessary prior to examination because it is not easy to maintain physical condition. In addition, its use is limited for hyperglycemia such as diabetes, etc. In contrast, the probe for labeling macrophages of the present disclosure does not require fasting because it has no metabolic limitation, and can be used for diagnosis of atherosclerosis without limitation even in case of diabetes because it has no relationship with the condition of other metabolism-related hormones. In addition, whereas the foci of the brain and heart cannot be diagnosed with FDG, the probe for labeling macrophages of the present disclosure does not have such a problem. Furthermore, whereas the selective diagnosis of the presence of proinflammatory M1 macrophages is impossible with FDG, the probe for labeling macrophages of the present disclosure allows more accurate diagnosis of inflammation.

Specifically, macrophages play a central role in removal of foreign or waste materials of the body and innate immunity through phagocytosis and also play an important role in the regulation of acquired immunity through antigen processing. It is also known that the increased activity or function of macrophages often leads to pathological conditions in the body.

The macrophages are differentiated from monocytes and have a variety of phenotypes depending on tissue microenvironment. Under the effect of lipopolysaccharides (LPS) and cytokines secreted by T lymphocytes such as interferon (IFN)-γ, they are differentiated into M1-type macrophages which are involved in tissue debridement and inflammatory response through secretion of inflammatory cytokines and phagocytosis. In contrast, under the environment where inflammatory cytokines such as IL-4 or IL-13 are dominant, they are differentiated into M2 macrophages which express mannose receptors, dectin-1, arginase, etc. and are involved in tissue repair. These phenotypes of macrophages are determined by surrounding inflammatory environments, but the overall mechanism that regulates the differentiation of monocytes to macrophages has not been elucidated yet.

That is to say, whereas M1 macrophages are more abundant during the early stages and mediate the clearance and recruitment of other effector cells, M2 macrophages predominate towards the end of inflammation and promote vascularization and new tissue formation. Therefore, the course of inflammation can be diagnosed more accurately by labeling macrophages, particularly M1-type macrophages.

The probe for labeling macrophages or a kit for imaging macrophages including the same generates image signals with specific optical characteristics distinguished from the environment for visualization of the structure of macrophages and the location, degree, duration, etc. of the expression of the CD80 of the macrophages. The probe for labeling macrophages and a kit for imaging macrophages including the same enable highly reliable biological imaging using the fluorescence and fluorescence switching by a radioisotope or a fluorescent dye bound to the carrageenan derivative, distinguished from the background noise by naturally occurring fluorescent materials existing in the body.

Accordingly, the probe for labeling macrophages or a kit for imaging macrophages including the same can diagnose and detect related diseases by labeling macrophages. The diseases that can be diagnosed include atherosclerosis, congestive heart failure, ischemic disease, restenosis, hypertension, fibrovascular disorders (diabetes, systemic erythematodes, etc.), neurodegenerative diseases (e.g., Alzheimer's disease, Huntington's disease, Parkinson's disease, spinocerebellar degeneration, amyotrophic lateral sclerosis, etc.), brain damage, cerebrovascular accidents (e.g., stroke, seizure, nerve injury and regeneration in the central nervous system, etc.), hematopoietic disorder, adult respiratory distress syndrome (ARDS), cancers (especially, leukemia including adult T-cell leukemia) and solid cancers, autoimmune disease, infections (e.g., HIV infection, AIDS, etc.), fibroproliferative disorders (e.g., psoriasis, etc.), chronic and acute inflammatory diseases (e.g., articular rheumatism, Crohn's disease, inflammatory bowel disease, etc.), glomerular disease, sepsis, transplant rejection, graft-versus-host disease, bone disease, pathological conditions of cardiac and other blood vessels characterized by deformable fibroplasia/inflammatory response, e.g. diseases characterized by infiltration of leukocytes into damaged sites such as oxygen- or glucose-deficient tissues (e.g., stroke, myocardial infarction, etc.), etc.

The fluorescent dye may be a fluorescent dye modified with a functional group. The functional group may be a thiocyanate (—SCN) or isothiocyanate (—NCS) group. The fluorescent dye may be one or more selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA and biotin.

The radioisotope may be one or more selected from a group consisting of C-11, F-18, Ga-67, Ga-68, Cu-64, I-123, I-124, I-125, Zr-89, In-111, Tc-99m, Y-90, Re-186, Re-188, Lu-177, Ac-225, At-211 and 1-131.

The probe for labeling macrophages or a kit for imaging macrophages including the same may further include a pharmaceutically acceptable carrier.

The carrier includes a carrier and a vehicle commonly used in the medical field. Specifically, it includes ion exchangers, alumina, aluminum stearate, lecithin, serum proteins (e.g., human serum albumin), buffers (e.g., phosphates, glycine, sorbic acid, potassium sorbate, or partial glyceride mixtures of saturated vegetable fatty acids), water, salts or electrolytes (e.g., protamine sulfate, disodium hydrogen phosphate, potassium hydrogen phosphate, sodium chloride or zinc salts), colloidal silica, magnesium trisilicate, polyvinylpyrrolidone, cellulose derivatives, polyethylene glycol, sodium carboxymethyl cellulose, polyacrylate, wax, polyethylene glycol, wool fat, etc., although not being limited thereto. The probe for labeling macrophages or a kit for imaging macrophages including the same may further include, in addition to the above-described ingredients, a lubricant, a wetting agent, an emulsifier, a suspending agent, a preservative, etc.

The probe for labeling macrophages or a kit for imaging macrophages including the same may be prepared into an aqueous solution for parenteral administration. Specifically, a buffer solution such as Hank's solution, Ringer's solution or physically buffered saline may be used. A substance for increasing viscosity such as sodium carboxymethyl cellulose, sorbitol or dextran may be added to an aqueous suspension for injection.

In another specific exemplary embodiment, the probe for labeling macrophages or a kit for imaging macrophages including the same may be in the form of a sterile injectable aqueous or oleaginous suspension. This suspension may be formulated according to techniques known in the art using a suitable dispersing or wetting agent (e.g., Tween 80) and a suspending agent. The sterile injectable preparation may also be a sterile injectable solution or suspension in a nontoxic, parenterally acceptable diluent or solvent (e.g., a solution in 1,3-butanediol). As a vehicle or a solvent, mannitol, water, Ringer's solution or an isotonic sodium chloride solution may be used.

In addition, a sterile, nonvolatile oil is commonly used as a solvent or a suspending medium. For this purpose, any nonvolatile oil including synthetic mono- or diglyceride may be used.

The probe for labeling macrophages or a kit for imaging macrophages including the same may be administered to an organism or a sample. An image may be acquired by detecting a signal emitted from the organism or the sample by a radioisotope or a fluorescent dye, and background noise may be removed by inducing photoconversion through UV radiation. This will enable the diagnosis of cancer and specific diseases, the research of the mechanism of biological signaling, the research of the differentiation of stem cells, etc. based on the fluorescence emission from a specific target site.

The term "sample" used herein refers to a tissue or a cell isolated from a subject to be diagnosed. The probe for labeling macrophages or a kit for imaging macrophages including the same may be injected to an organism or a sample via a route commonly used in the medical field. Parenteral administration is preferred. For example, it may be administered intravenously, intraperitoneally, intramuscularly, subcutaneously or topically. In addition, by adding the probe for labeling macrophages or a kit for imaging macrophages including the same to a culture of cells and observing binding to the CD80 of macrophages from among the cells, important information for research of macrophages, particularly M1-type macrophages, may be acquired.

The signal emitted from the probe for labeling macrophages or a kit for imaging macrophages including the same of the present disclosure may be detected by target imaging such as single-photon emission computed tomography (SPECT), positron emission tomography (PET), micro-PET, computed tomography (CT) or magnetic resonance imaging (MRI), or by using a device selected from a group consisting of a fluorescence microscope, a confocal fluorescence microscope, a spectrophotometer, a fluorescence analyzer, a CCD camera, a microscope for real-time monitoring of live cells (Delta Vision) and a combination thereof, which may be included in the kit for imaging macrophages.

Another aspect of the present disclosure relates to a method for preparing a probe for labeling macrophages, which includes:

a) a step of preparing a carrageenan-aldehyde having repeat units represented by Chemical Formulas 1 and 4 by reacting carrageenan having a repeat unit represented by Chemical Formula 1 with an oxidizing agent;

b) a step of substituting an aldehyde group of the carrageenan-aldehyde with a compound of Chemical Formula 2 or 3 by reacting the carrageenan-aldehyde prepared in the step a) with a compound represented by Chemical Formula 2 or Chemical Formula 3;

c) a step of reacting the substituted carrageenan derivative prepared in the step b) with a reducing agent; and d) a step of reacting the carrageenan derivative prepared in the step c) with a radioisotope or an isothiocyanate-modified fluorescent dye.

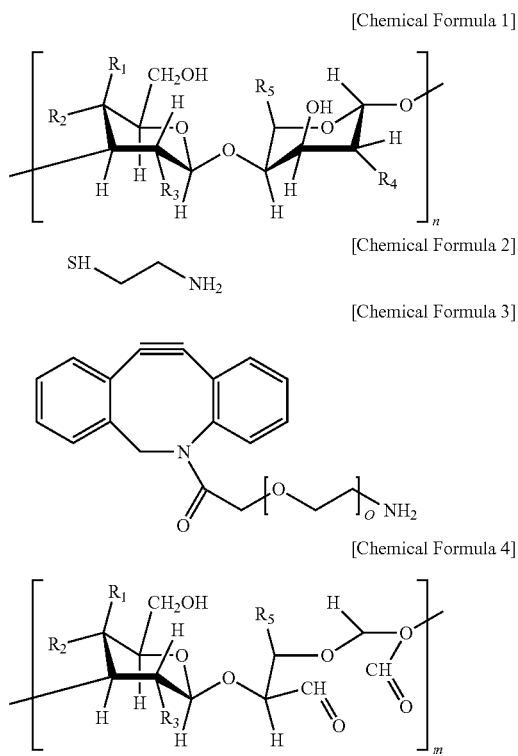

[Chemical Formula 1]

[Chemical Formula 2]

[Chemical Formula 3]

[Chemical Formula 4]

In the above chemical formulas, each of $R_1$ to $R_5$ is independently any one selected from a group consisting of —H, —OH, —CH$_3$, —CH$_2$OH, —COOH and —OSO$_3^-$, each of n and m is an integer from 1 to 10,000, and o is an integer from 1 to 10.

A detailed description of the preparation process of a carrageenan derivative including the steps a), b) and c) will be omitted since it has been described above regarding the preparation process of a carrageenan derivative including the steps 1), 2) and 3).

The radioisotope may be one or more selected from a group consisting of C-11, F-18, Ga-67, Ga-68, Cu-64, I-123, I-124, I-125, Zr-89, In-111, Tc-99m, Y-90, Re-186, Re-188, Lu-177, Ac-225, At-211 and I-131. Specifically, it may be Tc-99m. Tc-99m is preferred to obtain images by administering to the human body because it has a relatively short half-life of 6 hours and emits only y-rays of 140 keV, which have superior penetration ability with less toxicity to the human body.

When the radioisotope has a valence of +5, such as Tc-99m, it can coordinate with atoms having electron donor properties, such as nitrogen, sulfur, etc. Therefore, carrageenan consisting only of oxygen and atom cannot coordinate stably with Tc-99m. In contrast, the carrageenan derivative prepared as described above can coordinate stably with Tc-99m since it has such atoms as nitrogen, sulfur, etc. in the compound. Since Tc-99m has an oxidation state of +7 when eluted from a generator, it can be coordinated with a nitrogen- or sulfur-containing glucose derivative after reducing to +5 using a reducing agent. The radioisotopes 188 Re and 186 Re can be labeled with the same method.

The reducing agent may be any one selected from a group consisting of ascorbic acid, copper sulfate hydrate (CuSO$_4$.5H$_2$O), tin chloride hydrate (SnCl$_2$.2H$_2$O) and tin sulfate (SnSO$_4$). The reducing agent facilitates the labeling of the carrageenan derivative with a radioisotope by reducing the radioisotope.

The prepared probe for labeling macrophages is advantageous in that labeling efficiency is not decreased when it is used for imaging of macrophages. The radioisotope included in the molecular structure may be imaged using an X-ray source.

The probe for labeling macrophages according to the present disclosure can form a stable bond with a radioisotope used in a contrast agent since the carrageenan derivative acts as a metal chelating agent. See, for example, Reaction Scheme 2 in Example 1 as an example.

Meanwhile, the fluorescent dye is a material which, after being excited by light of a specific wavelength, emits the absorbed energy as light of a specific wavelength and returns to its ground level. It may be one or more selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA and biotin.

The probe for labeling macrophages is prepared by reacting the carrageenan derivative with the fluorescent dye, and the fluorescent dye may be one chemically modified with one or more functional group.

The fluorescent dye modified with a functional group may be modified with a thiol (—SH), an amine group (—NH$_2$), a cyanide group (—CN), an isocyanide group (—CNO), a thiocyanate group (—SCN), an isothiocyanate group (—NCS), a disulfide group (—SS—) or an azide group (—N$_3$). Specifically, it may be may be modified with an isothiocyanate group.

A probe for labeling macrophages with a stable structure may be prepared as the modified fluorescent dye forms a stable thiourea by reacting with the mercapto group of the carrageenan derivative.

The probe for labeling macrophages formed through the process described above from binding of the carrageenan derivative with one or more fluorescent dye or radioisotope can target/label inflammation-relates macrophages, particularly M1-type macrophages, for live cell imaging and diagnostic imaging.

Another aspect of the present disclosure relates to a method for preparing a probe for labeling macrophages, which includes i) a step of preparing carrageenan-aldehyde having repeat units represented by Chemical Formulas 1 and 4 by reacting carrageenan having a repeat unit represented by Chemical Formula 1 with an oxidizing agent;

ii) a step of substituting an aldehyde group of the carrageenan-aldehyde with a compound of Chemical Formula 3 by reacting the carrageenan-aldehyde prepared in the step i) with a compound represented by Chemical Formula 3;

iii) a step of reacting the substituted carrageenan derivative prepared in the step ii) with a reducing agent; and iv) a step of conducting copper-free click reaction of the carrageenan derivative prepared in the step iii) with an azide compound represented by Chemical Formula 5.

A detailed description of the preparation process of a carrageenan derivative including the steps i), ii) and iii) will be omitted since it has been described above regarding the preparation process of a carrageenan derivative including the steps a), b) and c).

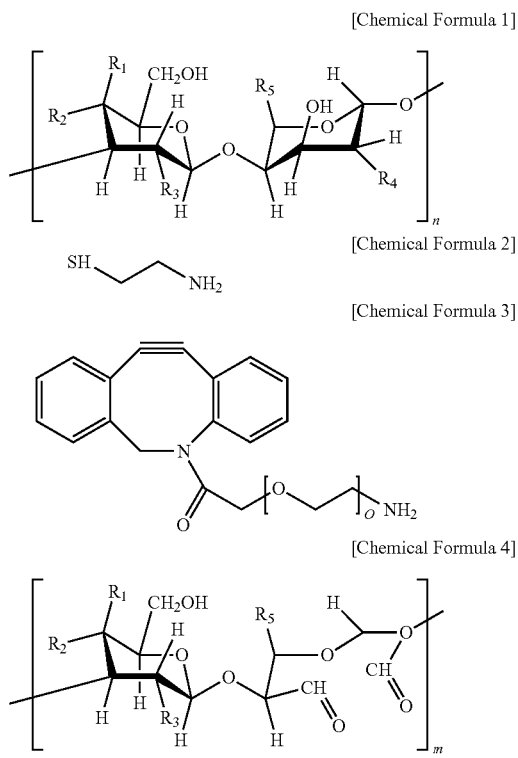

[Chemical Formula 1]

[Chemical Formula 2]

[Chemical Formula 3]

[Chemical Formula 4]

In the above chemical formulas, each of $R_1$ to $R_5$ is independently is any one selected from a group consisting of —H, —OH, —CH$_3$, —CH$_2$OH, —COOH and —OSO$_3^-$, each of n and m is an integer from 1 to 10,000, and o is an integer from 1 to 10.

[Chemical Formula 5]

In Chemical Formula 5,

A is any one selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA, biotin, C-11, F-18, Ga-67, Ga-68, Cu-64, I-123, I-124, I-125, Zr-89, In-111, Tc-99m, Y-90, Re-186, Re-188, Lu-177, Ac-225, At-211 and I-131.

Specifically, the probe for labeling macrophages may be prepared quickly with high radiochemical yield by conducting copper-free click reaction of the carrageenan derivative with an azide compound labeled with a fluorescent dye or a radioisotope (Chemical Formula 5).

More specifically, since the prepared carrageenan derivative contains dibenzocyclooctyne (DBCO) represented by Chemical Formula 3, copper-free click reaction with an azide group (—N$_3$)-containing compound represented by Chemical Formula 5 can be conducted in short time with high yield. Therefore, the carrageenan derivative is not specially limited as long as it is one substituted with a dibenzocyclooctyne compound (Chemical Formula 3), and the probe for labeling macrophages may be prepared by easily binding a radioisotope or a fluorescent dye using the azide compound labeled with a fluorescent dye or a radioisotope of the present disclosure.

The azide compound labeled with a fluorescent dye or a radioisotope may be synthesized according to any known synthesis method without special limitation.

In addition, the carrageenan derivative of the present disclosure used in the step iv) of the present disclosure is not specially limited as long as copper-free click reaction can occur using the azide compound labeled with a fluorescent dye or a radioisotope of the present disclosure (Chemical Formula 5). Specifically, a carrageenan derivative containing dibenzocyclooctyne may be used.

By conducting copper-free click reaction of the azide compound labeled with a fluorescent dye or a radioisotope with the carrageenan derivative substituted with dibenzocyclooctyne, a carrageenan derivative wherein a fluorescent dye or a radioisotope is bound/conjugated (probe for labeling macrophages) is obtained.

In another aspect, the present disclosure provides a method for providing information about the location of macrophages, which includes a step of administering the probe for labeling macrophages to an isolated biological sample and identifying the location where a signal selected from a group consisting of color, near infrared fluorescence, radiation and a combination thereof is generated.

In the present disclosure, the term "subject" refers to a living organism where inflammation-related symptoms and lesions have occurred due to inflammation, to which the probe or kit for labeling macrophages of the present disclosure can be administered.

When the probe for labeling macrophages provided by the present disclosure is administered into the living body, it can bind to inflammation-related macrophages, particularly M1-type macrophages, in the body and label the location of the macrophages through color, near infrared fluorescence, radiation or a combination thereof. Since the location, size, etc. of macrophages can be detected in real time by detecting the label. Therefore, inflammation-related diseases can be diagnosed and the state and progression of inflammation can be monitored.

Furthermore, since the probe for labeling macrophages of the present disclosure can selectively label macrophages regardless of metabolism when compared with other complexes conjugated with dyes, it can easily detect the location of macrophages even in the foci of the brain and heart without limitation by a patient's condition.

MODE FOR INVENTION

Hereinafter, the present disclosure will be described in more detail through examples, etc. However, it should not be construed that the scope and content of the present disclosure are reduced or limited by the examples, etc. In addition, it is obvious that those having ordinary knowledge can easily carry out the present disclosure for the matters for which experimental results are not presented specifically based on the content of the present disclosure including the examples, etc. and that such changes and modifications belong to the scope of the appended claims.

The experimental results presented below are only representative experimental results of examples and comparative examples.

Preparation Example 1. Synthesis of Carrageenan Derivative
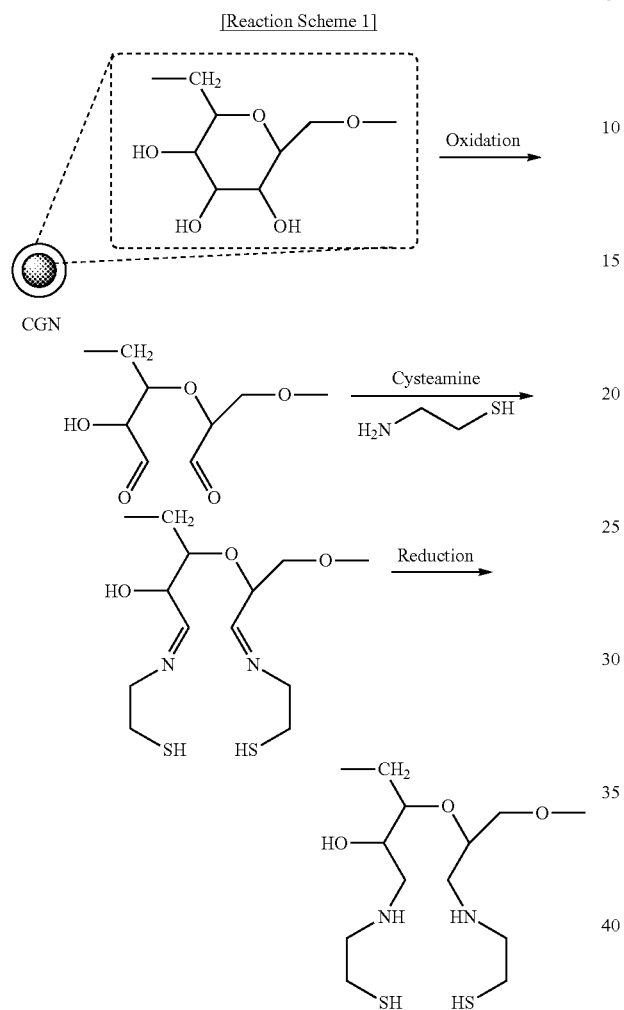
[Reaction Scheme 1]
Reaction Scheme 1 shows a procedure of synthesizing a carrageenan derivative acting as a ligand of CD80 of macrophages by oxidizing, substituting and reducing carrageenan (CGN).

Prior to synthesis, physical property (solubility) was investigated using a 10 mg/mL CGN solution (in DW). Aggregation was confirmed by dynamic light scattering (DLS).

Based on the physical property, 10 mL of a 2.5 mg/mL CGN aqueous solution was prepared. 2 mL of the CGN aqueous solution was used for reaction. After adding 0.02 mmol (4.3 mg) of sodium periodate as an oxidizing agent to the CGN aqueous solution, carrageenan-aldehyde was prepared by opening the ring structure of carrageenan by performing oxidation at room temperature for 30 minutes. The carrageenan-aldehyde was filtered with distilled water using a PD-10 column. Then, after adding 0.02 mmol (1.5 mg) of cysteamine to the filtered solution, carrageenan with the aldehyde group of the carrageenan-aldehyde substituted with a cysteamine group was synthesized by conducting reaction at room temperature for 1 hour. Then, after adding 0.02 mmol (0.75 mg) of sodium borohydride to the carrageenan substituted with a cysteamine group as a reducing agent, a carrageenan derivative was synthesized by conducting reaction in an ice bath for 1 hour. After neutralizing the carrageenan derivative by adding concentrated HCl, the PD-10 column was filtered using distilled water. The compounds were used in equimolar amounts.

Preparation Example 2. Synthesis of Carrageenan Derivative from λ-Carrageenan

[Reaction Scheme 2]

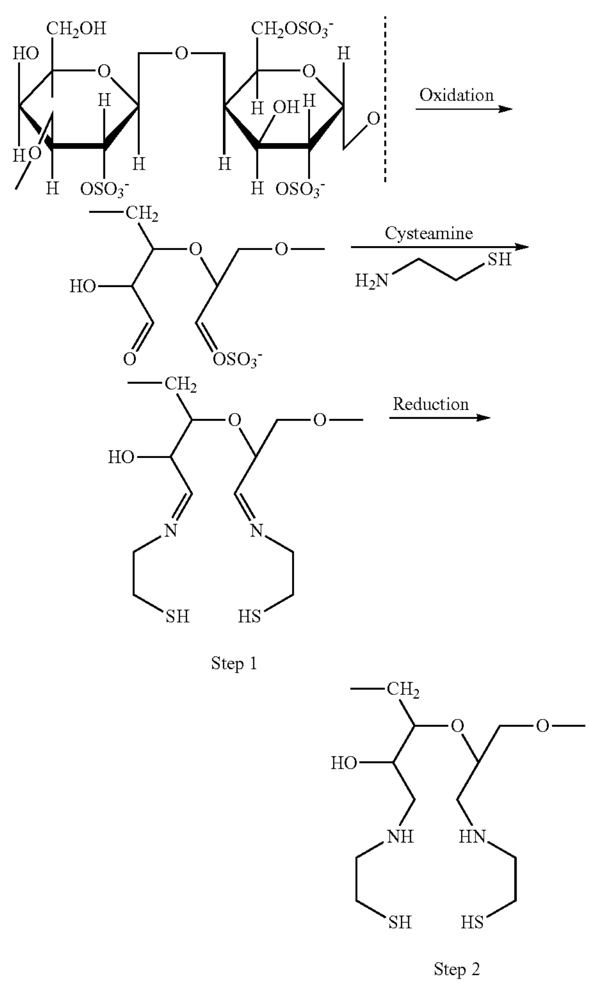

Reaction Scheme 2 shows a procedure of synthesizing a carrageenan derivative acting as a ligand of CD80 of macrophages by oxidizing, substituting and reducing A-carrageenan. A-Carrageenan is a polymer having three sulfate groups per two sugar units.

A mixture of $NaIO_4$ (3.9 mg, 0.018 mmol) and $H_2SO_4$ (2 μL) was added to 5 mL of the λ-carrageenan solution (7 mg/mL). After stirring the reaction mixture at room temperature for 30 minutes, the reaction mixture was purified using a PD-10 column (Sephadex™ G-25 Medium, GE Healthcare Bio-Sciences Corp, NJ, USA). Carrageenan-aldehyde was prepared by recovering 1 mL of fractions serially 3 times. 2.5 mL of a carrageenan-aldehyde solution was prepared by dissolving the carrageenan-aldehyde in distilled water. Then, 100 molar equivalents excess cysteamine (2.1 mg, 0.018 mmol) was mixed based on the oxidized A-carrageenan contained in the solution. After stirring the mixture at room temperature for 60 minutes, sodium borohydride (NaBH$_4$, 0.687 mg, 0.018 mmol) was added. A carrageenan derivative was synthesized by stirring the reaction mixture in an ice-cold water bath for 60 minutes.

Preparation Example 3. Synthesis of DBCO-Carrageenan Derivative

Unlike the methods for preparing a carrageenan derivative of Preparation Examples 1 and 2, a carrageenan derivative for preparation of a probe for labeling macrophages may be prepared through click reaction.

A DBCO-carrageenan derivative was synthesized in the same manner as in Preparation Example 1, except that a compound represented by Chemical Formula 3 was added instead of cysteamine.

[Chemical Formula 3]

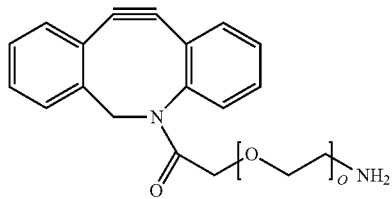

In Preparation Example 3, a compound represented by Chemical Formula 3 with o being 1 was used.

Example 1. Tc-99m-Labeled Probe for Labeling Macrophages

Reaction Scheme 3 shows a process of preparing a carrageenan derivative (also referred to as modified carrageenan) as described in Preparation Example 1 and labeling the same with Tc-99m to synthesize a probe for labeling macrophages.

First, a 2.5 mg/mL SnCl$_2$ solution was prepared and a 2.5 mg/mL solution of the carrageenan derivative synthesized in Preparation Example 1 was prepared. In order to prevent colloidal phenomenon, 0.1 M HCl was used as a solvent. After adding the SnCl$_2$ solution (10 μL) to 200 μL of the carrageenan derivative solution synthesized in Preparation Example 1, $^{99m}$Tc (20 μL, 140 μCi in saline) was added and the mixture solution was vortexed. After conducting reaction at room temperature for 20 minutes, radio-thin-layer chromatography (radio-TLC) was performed using a mixture of saline and citric acid as an eluent. The reaction was conducted for 1 hour (up to 2 hours). In addition, chromatography was performed by adding citrate, saline and acetone to the eluent.

Example 2. RITC-Labeled Probe for Labeling Macrophages

[Reaction Scheme 4]

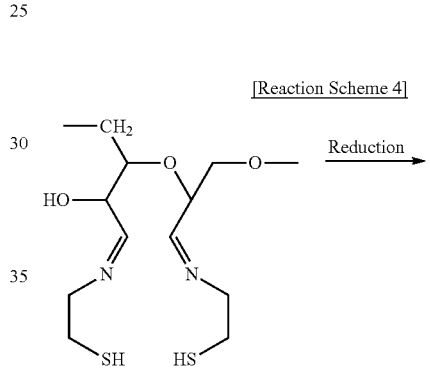

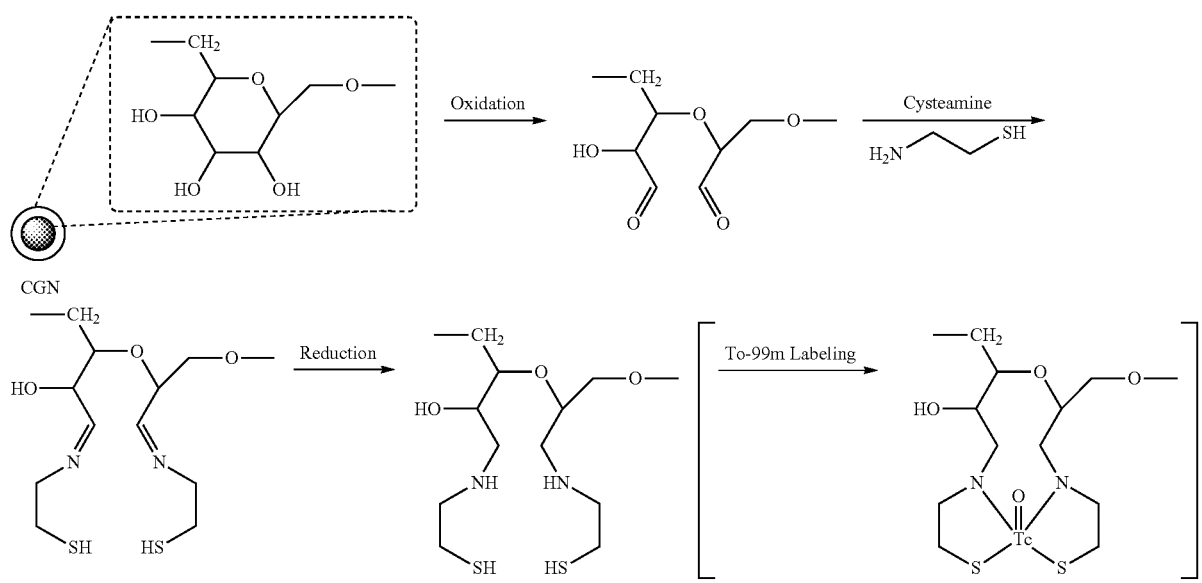

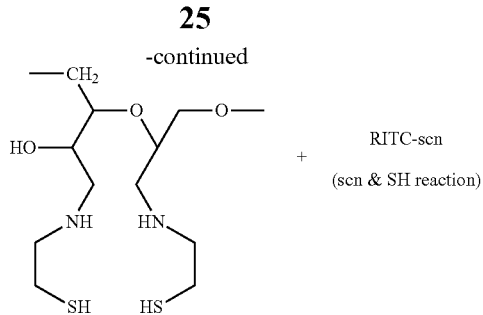

Reaction Scheme 4 shows a procedure of labeling the carrageenan derivative synthesized in Preparation Example 2 with RITC. In order to label the carrageenan derivatives (prepared in Preparation Example 1 and Preparation Example 2) with RITC, RITC modified with isothiocyanate has to be used. That is to say, a probe for labeling macrophages is prepared via a mechanism whereby the mercapto (sulfhydryl) group of the carrageenan derivative reacts with the isothiocyanate of RITC to form stable thiourea. The synthesis procedure will be described specifically.

An RITC-labeled probe for labeling macrophages was prepared by stirring the carrageenan derivative synthesized in Preparation Example 2 together with a sodium carbonate buffer (pH=9.5) and scn-RITC (1 mg, 0.0018 mmol), reacting overnight and then purifying with PBS. The RITC concentration of the RITC-labeled probe for labeling macrophages was investigated using nano-drops (Test Example 2).

Example 3. Probe for Labeling Macrophages Prepared Through Click Chemical Reaction After dissolving 7 nmol (1 mg) of the DBCO-carrageenan derivative prepared in Preparation Example 3 and 70 nmol (0.02 mg) of an azide compound represented by Chemical Formula 5 (purchased from Click Chemistry Tools) in 0.1 mL of distilled water, a probe for labeling macrophages with a fluorescent dye or a radioisotope introduced was obtained easily by conducting copper-free click chemical reaction. In this example, an azide compound represented by Chemical Formula 5 with A being Cy3 or NOTA was used.

[Chemical Formula 5]

When an isotope or a fluorescent dye is introduced as in Examples 1 and 2, the carrageenan derivative has to be prepared separately depending on purposes. However, when a probe for labeling macrophages is prepared through click chemical reaction, not only an isotope but also a fluorescent dye can be introduced by using the carrageenan derivative of Preparation Example 3.

Test Example 1. Analysis of Labeling Efficiency of Probe for Labeling Macrophages Prepared in Example 1

$^{99m}$Tc labeling efficiency was investigated to confirm the synthesis result of the probe for labeling macrophages prepared in Example 1.

Figure 1B:
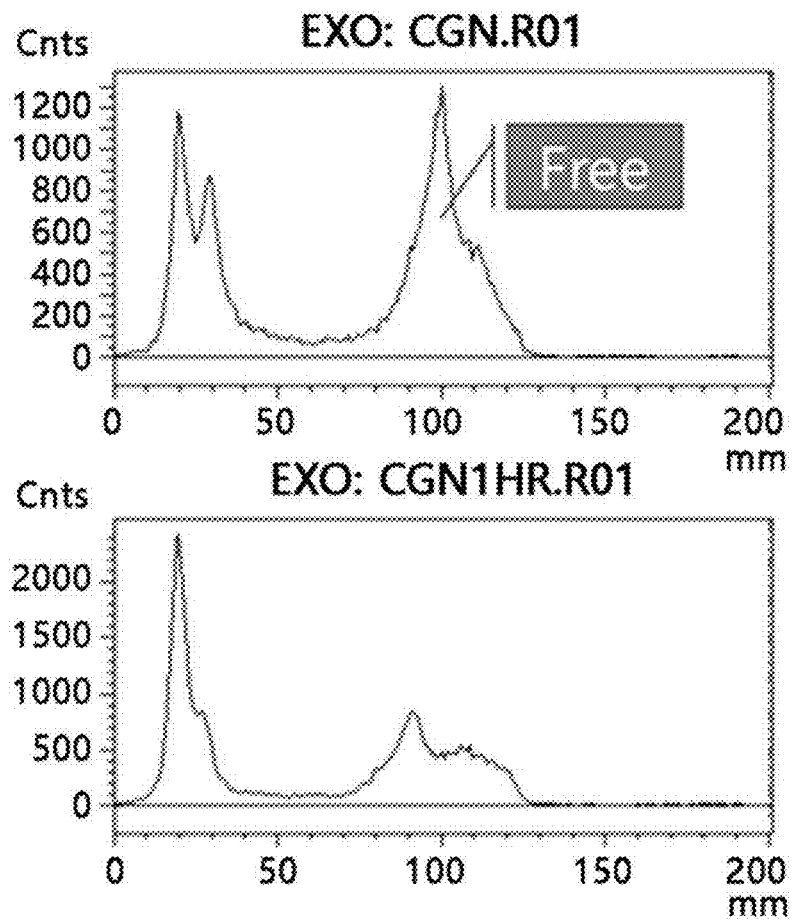
FIG. 1 shows a result of conducting instant thin layer chromatography (iTLC) to confirm the synthesis of a Tc-99m-labeled probe for labeling macrophages prepared in Example 1.
Figure 1C:
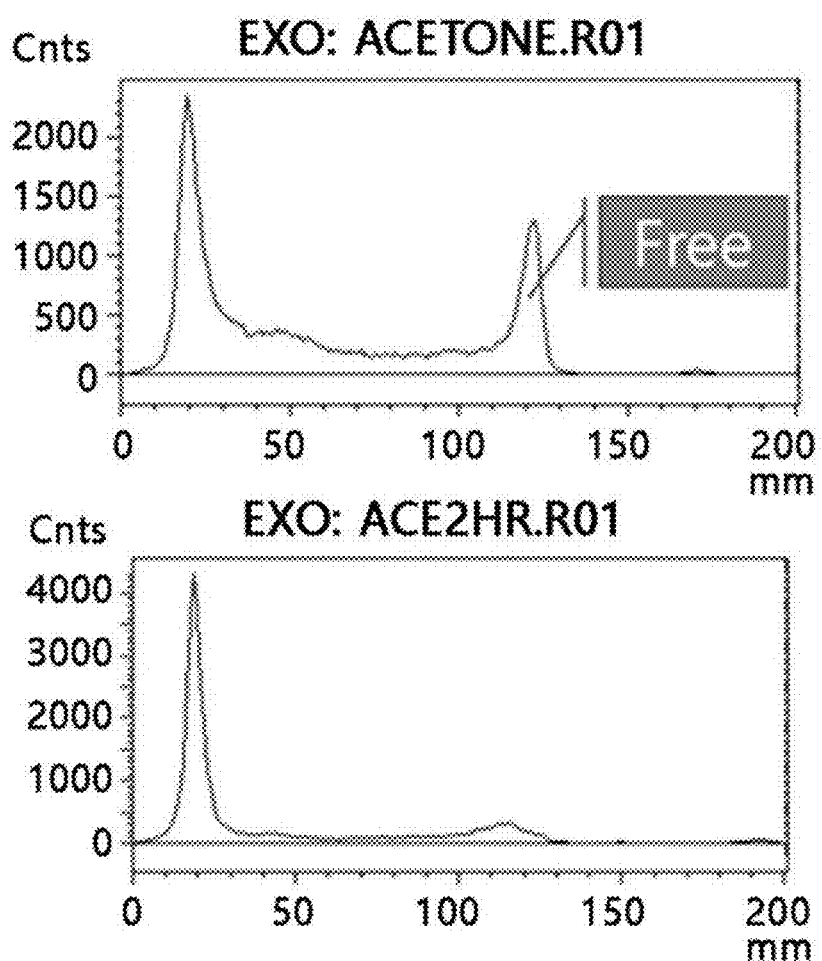

FIG. 1 shows a result of conducting instant thin layer chromatography (iTLC) to confirm the synthesis of the Tc-99m-labeled probe for labeling macrophages prepared in Example 1. Citric acid, saline and acetone were used as eluents and labeling efficiency was >90%.

As shown in FIG. 1, labeling efficiency was >90% when instant thin-layer chromatography (iTLC)-silica gel (SC) was conducted using citric acid, saline and acetone for 5 minutes (free: free form of $^{99m}$Tc). It can be seen that 90% or more of $^{99m}$Tc is bound to the carrageenan derivative since the peak indicating the presence of free-form $^{99m}$Tc has almost disappeared.

Test Example 2. Analysis of Probe for Labeling Macrophages Prepared in Example 2

RITC labeling efficiency was investigated to confirm the synthesis result of the probe for labeling macrophages prepared in Example 2. Since peaks were not observed distinctly, the efficiency was calculated using a PD-10 column.

Figure 2:
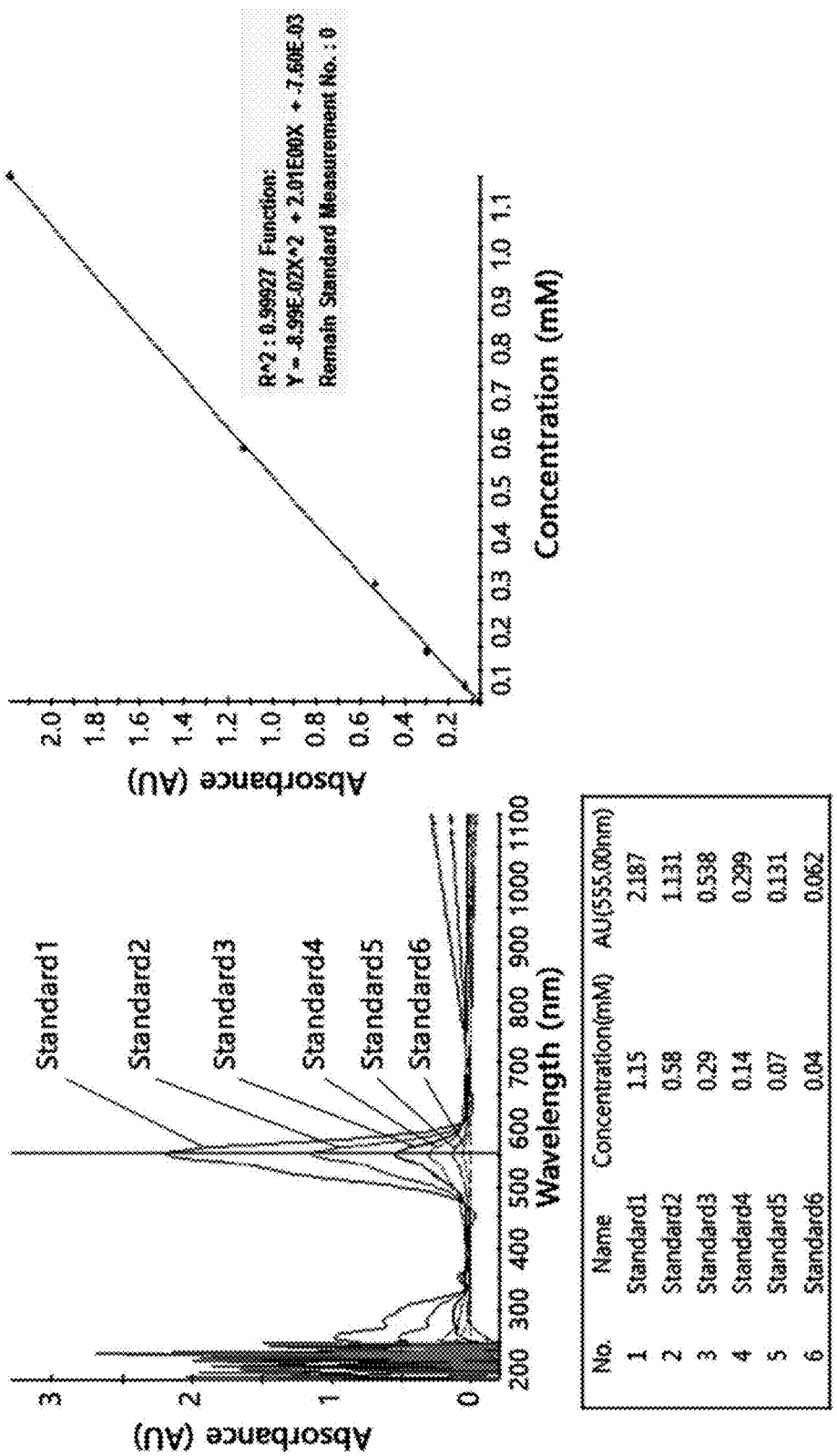
FIG. 2 shows a UV calibration curve depending on the concentration of RITC (1-0.01 mg/mL).
Figure 3:
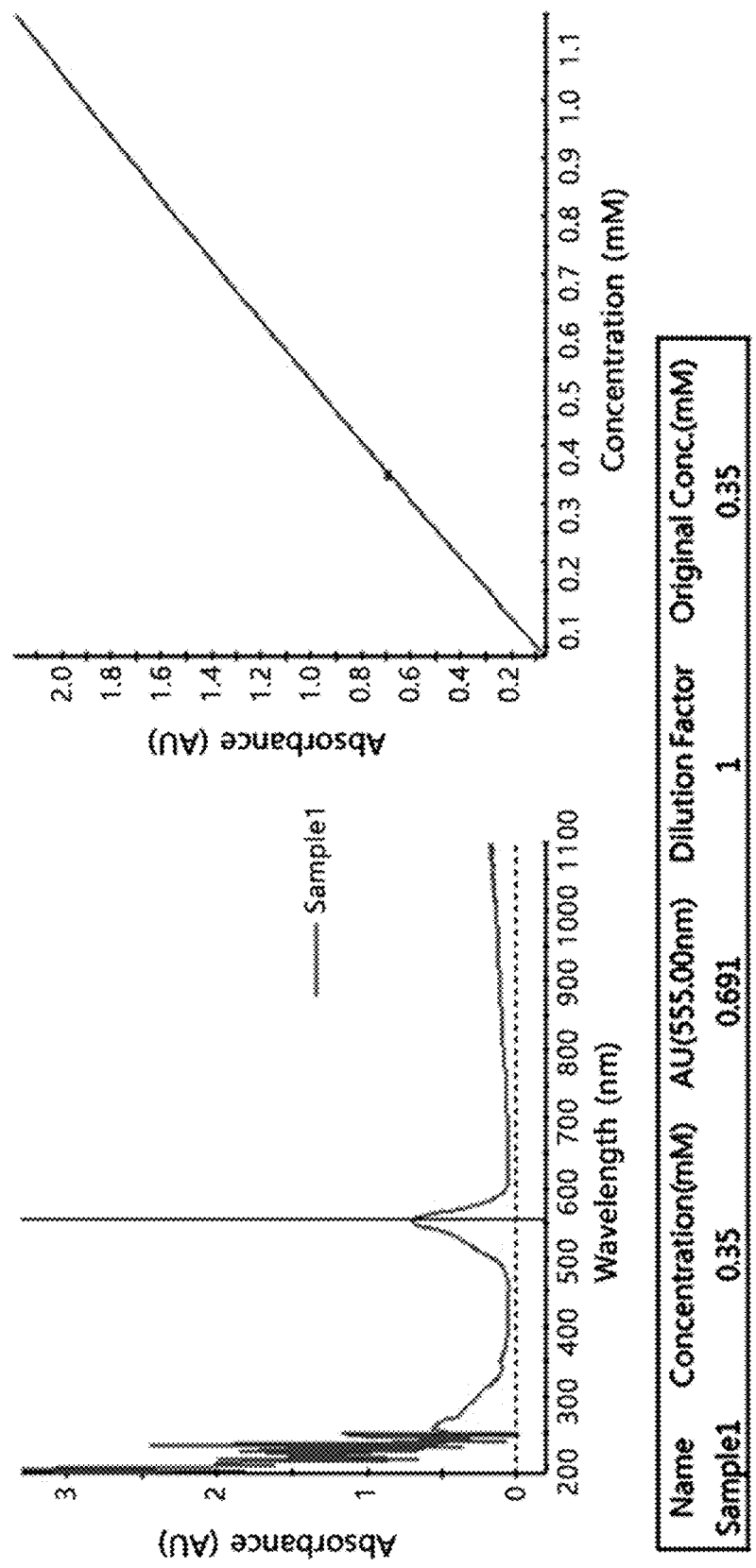
FIG. 3 shows the UV absorbance of an RITC-labeled probe for labeling macrophages prepared in Example 2.

FIG. 2 shows the UV calibration curve depending on the concentration of RITC (1-0.01 mg/mL), and FIG. 3 shows the UV absorbance of the RITC-labeled probe for labeling macrophages prepared in Example 2.

The calibration curve of FIG. 2 was obtained by measuring UV absorbance after nano-dropping solutions in which RITC was diluted at concentrations from 1 mg/mL to 0.01 mg/mL, in order to confirm the preparation of probe for labeling macrophages through binding of RITC to the carrageenan derivative. As a result of measuring the UV absorbance of the probe for labeling macrophages prepared in Example 2 and fitting the result to the calibration curve of FIG. 2, it was confirmed that RITC was bound to the carrageenan derivative since the concentration of RITC in the probe for labeling macrophages of Example 2 was 0.2 mg/m L.

Test Example 3. MALDI-TOF/TOF MS Analysis of Probe for Labeling Macrophages Prepared in Example 2

MALDI-TOF/TOF MS analysis was conducted to determine the number of carrageenan-conjugated cysteamine (carrageenan derivative of Preparation Example 2) and RITC units in the RITC-labeled probe for labeling macrophages prepared in Example 2.

First, after mixing a fraction of the sample solution (10 μL) with a saturated solution of a-cyano-4-hydroxycinnamic acid (CHCA in a mixture of acetonitrile and water containing 0.1% TFA (1:1, v/v), 1 μL of the mixture solution was spotted on a MALDI plate and then dried completely at room temperature. Then, the plate was analyzed using a mass analyzer, and the spectrum for each spot was collected. The measurement was made in a linear mode with an acceleration voltage of 25 kV. The spot was treated with a 337-nm nitrogen laser. 20 laser shots were taken for each scan, and a total of 125 scans were made. The average molecular weights of the probe for labeling macrophages prepared in Example 2 (i.e., the modified carrageenan compound) and the λ-carrageenan (FIG. 4) were calculated by averaging the result of 2500 laser shots. The result is shown in Table 1.

Figure 5:
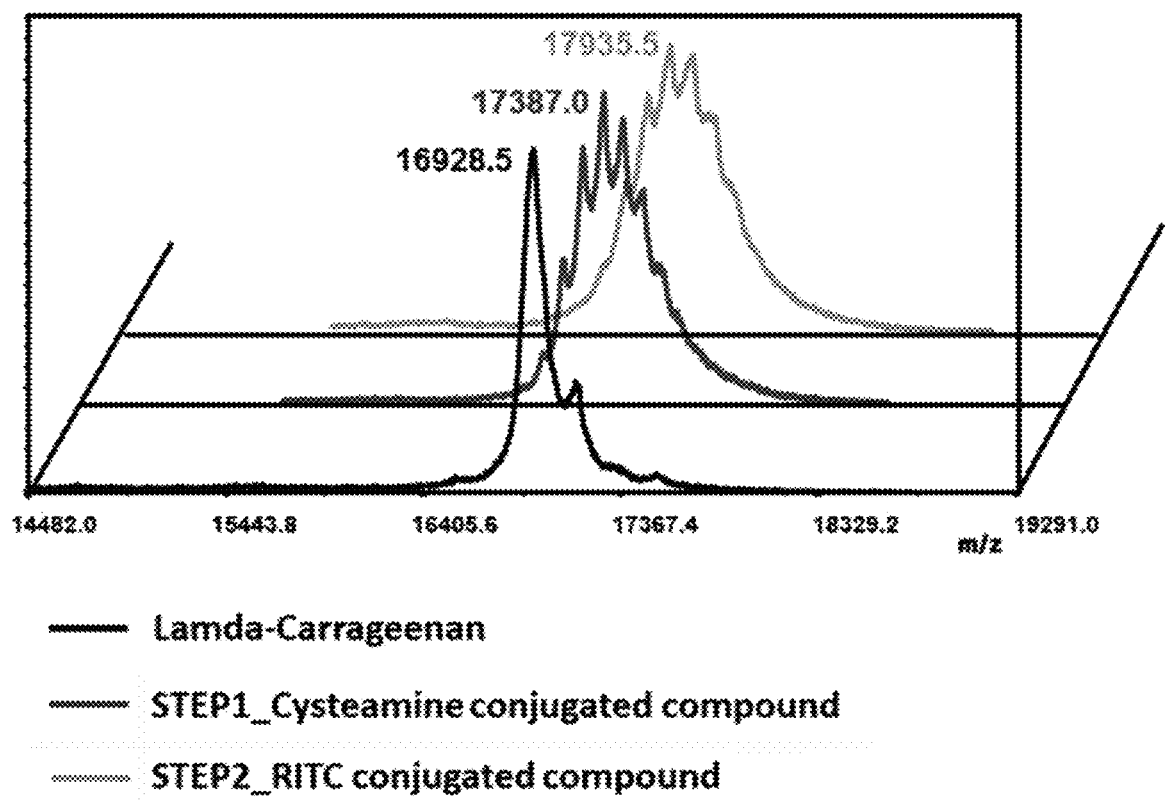
FIG. 5 shows MALDI-TOF results for A-carrageenan, a carrageenan derivative of Preparation Example 2 and an RITC-labeled probe for labeling macrophages of Example 2.
Figure 6:
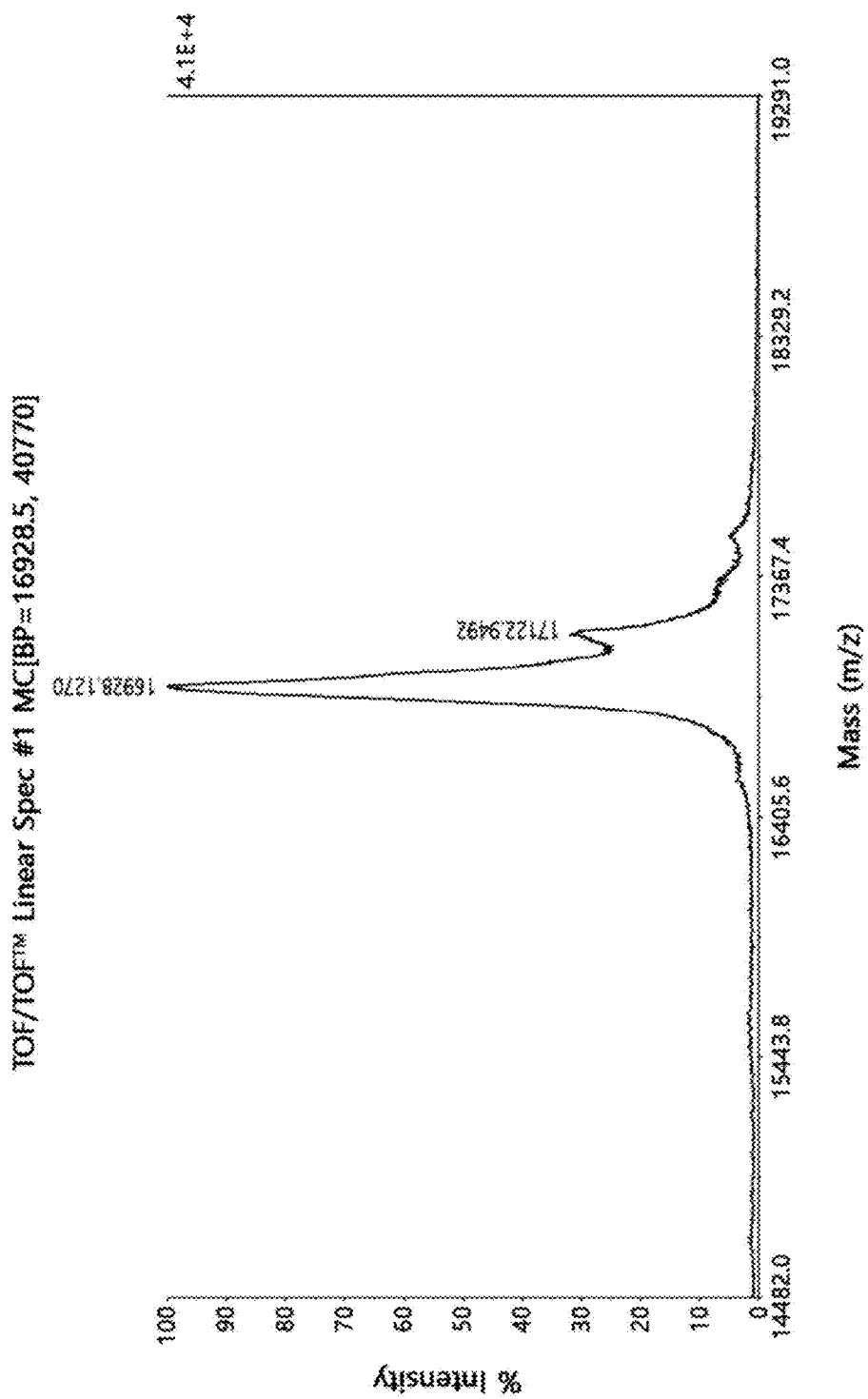
FIG. 6 shows the MALDI-TOF raw data of A-carrageenan.
Figure 7:
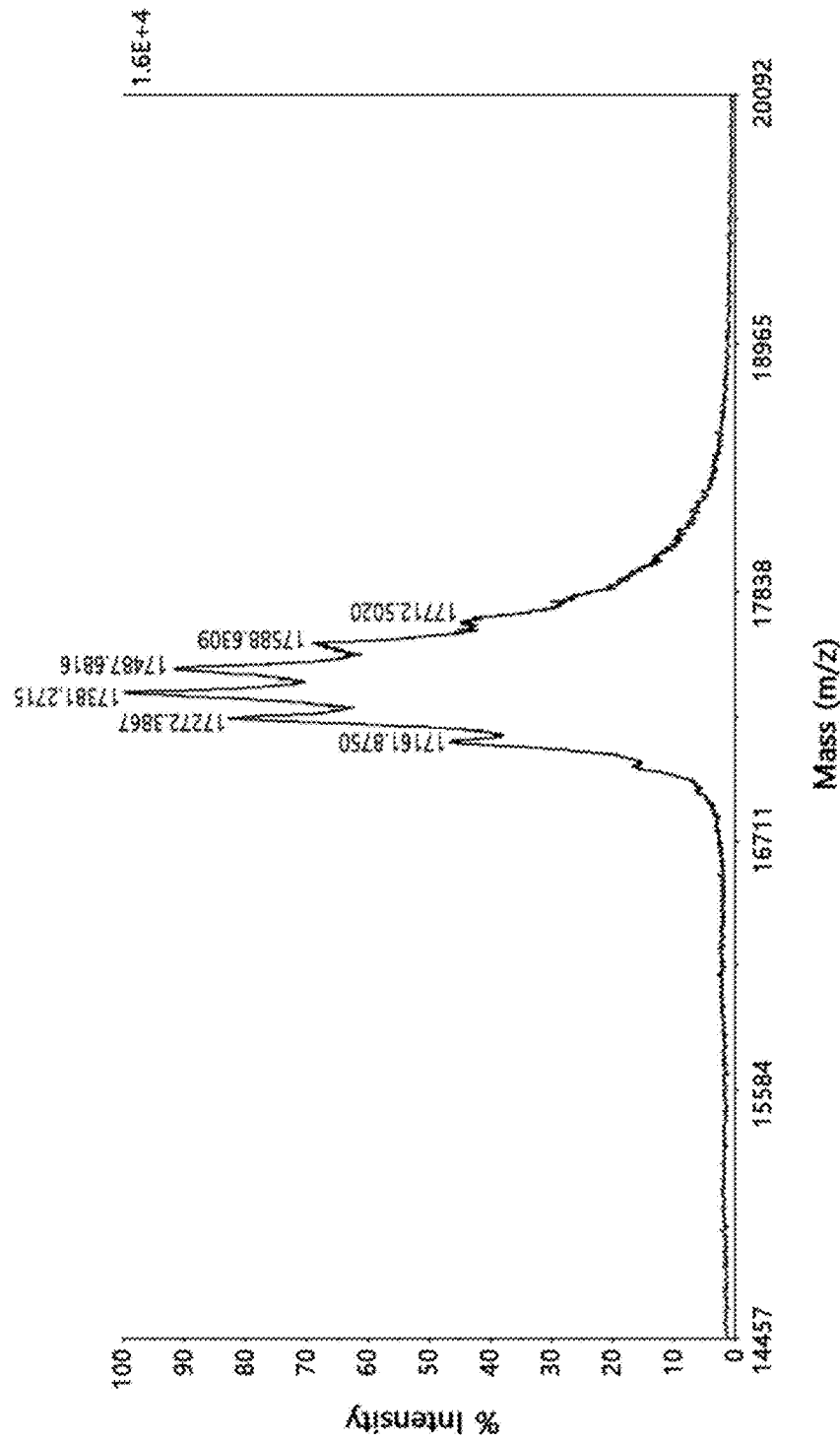
FIG. 7 shows the MALDI-TOF raw data of a carrageenan derivative of
Preparation Example 2.
Figure 8:
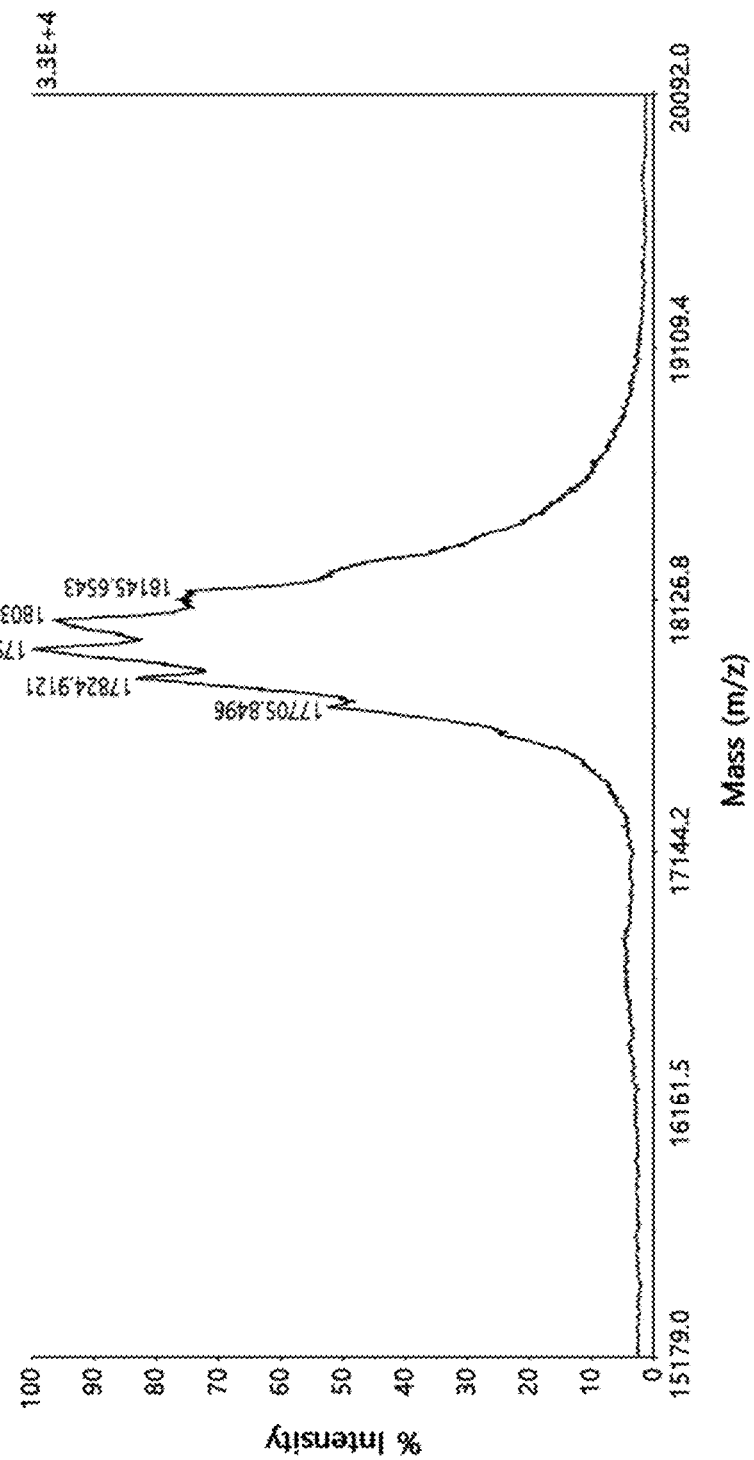
FIG. 8 shows the MALDI-TOF raw data of an RITC-labeled probe for labeling macrophages of Example 2.

FIG. 5 shows MALDI-TOF results for the λ-carrageenan, the carrageenan derivative of Preparation Example 2 and the RITC-labeled probe for labeling macrophages of Example 2, FIG. 6 shows the MALDI-TOF raw data of the λ-carrageenan, FIG. 7 shows the MALDI-TOF raw data of the carrageenan derivative of Preparation Example 2, and FIG. 8 shows the MALDI-TOF raw data of the RITC-labeled probe for labeling macrophages of Example 2.

TABLE 1

| Type | MW (mean) | Molecular weight of unit | Number |
|---|---|---|---|
| λ-Carrageenan | 16928.5 | 579.5/carrageenan | 29-30 per polymer |
| Carrageenan derivative of Preparation Example 2 | 17387.0 | 77.15/cysteamine | 5.94 ((Preparation Example 2 - λ-carrageenan)/77.15) |
| RITC-labeled probe for labeling macrophages of Example 2 | 17935.5 | 389.38/RITC-SCN | 1.40 ((Example 2 - Preparation Example 2)/389.38) |

MALDI-TOF-based molecular weight

According to Table 1 and FIGS. 5-8, the molecular weight of a carrageenan unit was 579.5 g/mol, and the molecular weight of the carrageenan polymer consisting of 29-30 unit compounds was 16928.5 g/mol. It can be seen that the molecular weight of the carrageenan derivative of Preparation Example 2 (cysteamine-carrageenan) was increased to 17387.0 g/mol as 5.94 cysteamines (77.15 g/mol) were attached per carrageenan polymer on average.

The molecular weight of the RITC-labeled probe for labeling macrophages prepared in Example 2 was increased to 17935.5 g/mol as 1.4 RITC-SCNs (389.38 g/mol) were attached per the carrageenan-cysteamine polymer on average.

That is to say, the probe for labeling macrophages according to the present disclosure specifically has 1-20 cysteamine-modified carrageenan units per 29-30 λ-carrageenan units on average and has 1-10 RITC-labeled carrageenan units on average. More specifically, it has 5-10 cysteamine-modified carrageenan units per 29-30 λ-carrageenan units on average and has 1-5 RITC-labeled carrageenan units.

Test Example 4. Analysis of Targeting Activity of Probe for Labeling Macrophages Prepared in Example 2 In Vitro It was investigated whether the probe for labeling macrophages prepared in Example 2 actually labels macrophages. The assessment was performed as follows.

First, Raw264.7 cells were dispensed onto an 8-well chamber slide, with about 5000 cells per well. After washing with a PBS buffer solution, the cells were fixed by treating with ice-cold methanol (MeOH) for 15 minutes. Then, after washing once again with a PBS buffer solution, each well was treated with the probe for labeling macrophages prepared in Example 2 (RITC-CGN) at different concentrations or a standard RITC solution (standard) for 30 minutes. After the reaction was completed, each well was washed with a PBS buffer solution for 150 seconds and then observed with a fluorescence microscope.

Figure 9:
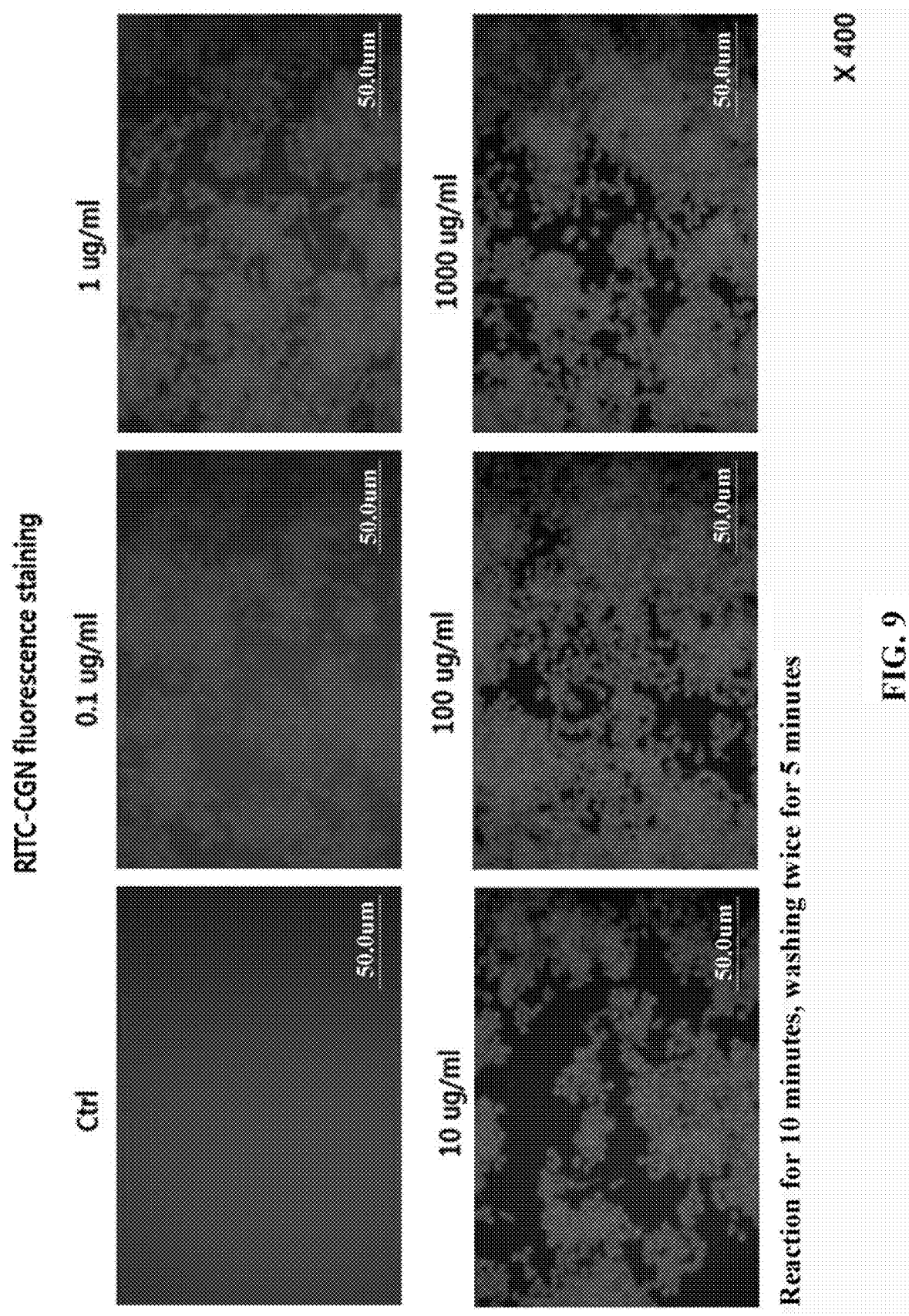
FIG. 9 shows the fluorescence microscopic images of activated white blood cells (Raw264.7) obtained after treating with a probe for labeling macrophages prepared in Example 2 (RITC-CGN) at various concentrations or a standard RITC solution.

The probe for labeling macrophages prepared in Example 2 (RITC-CGN) was diluted to concentrations of 0.1, 1, 10 and 100 μg/mL, as indicated in FIG. 9. In the figure, 1000 μg/mL indicates the standard RITC solution with a concentration of 1000 μg/mL, which was diluted with a PBS buffer solution (pH 9.5, 0.1 M sodium carbonate buffer). Ctrl indicates untreated RaW264.7 cells.

FIG. 9 shows the fluorescence microscopic images of the activated white blood cells (Raw264.7) obtained after treating with the probe for labeling macrophages prepared in Example 2 (RITC-CGN) at various concentrations or the standard RITC solution.

As shown in FIG. 9, it was confirmed that the nonspecific attachment of the probe for labeling macrophages of Example 2 (RITC-CGN) to the white blood cells in vitro is increased in a concentrate-dependent manner.

Specifically, for normal cells, RITC can be easily attached because many amine ($NH_2$) groups are present on the cell surface. However, since probe for labeling macrophages of the present disclosure (RITC-CGN) has chemically stable thiourea groups instead of the amine groups, RITC is not attached any more to the membrane of non-target cells. In addition, since the probe for labeling macrophages according to the present disclosure contains the carrageenan derivative which acts as a ligand for CD80 of target macrophages, only the macrophages having CD80 on the cell membrane surface are labeled by the probe for labeling macrophages of the present disclosure, and normal cells are not labeled by the probe for labeling macrophages of the present disclosure.

Test Example 5. Analysis of Targeting Activity of Probe for Labeling Macrophages Prepared in Example 2 for M1 Macrophages In Vitro 1) Test Groups (0.001 μg/mL Lipopolysaccharides)

Raw264.7 cells were dispensed onto an 8-well chamber slide, with about 5000 cells per well. After culturing for 1-2 days and then adding a 0.001 μg/mL LPS (inflammation-inducing materials) solution to each well, the cells were cultured for 24 hours. The LPS solution was prepared by mixing in an RPMI medium containing 10% FBS and 1% antibiotic-antifungal solution, and a final volume of 200 μL was added.

Then, after removing the culture medium from each well and washing with a PBS buffer solution, the cells were fixed by treating with ice-cold methanol for 15 minutes. Then, the cells were washed with a PBS buffer solution once for 5 minutes and then treated with blocking antibodies for 1 hour. As the antibodies, TLR4 (Abcam, ab47093) and CD80 (Novus, B7-1, AF740) were treated at 0.025 μg/μL, 0.005 μg/μL or 0.01 μg/μL, respectively.

Then, after washing each well once with a PBS buffer solution for 5 minutes, the probe for labeling macrophages prepared in Example 2 (RITC-CGN, 0.5 mg/mL based on the carrageenan derivative) was treated for 20 minutes. Then, after washing twice with PBS for 3 minutes and pouring 100-200 μL of a PBS buffer solution, the well was observed with a fluorescence microscope.

2) Negative Control Group (No Lipopolysaccharide)

In order to investigate whether the targeting activity is exhibited for cells in which inflammation did not occur (negative control group), non-LPS-treated Raw264.7 cells (no lipopolysaccharide) were treated in the same manner as in 1).

Then, after washing each well once with a PBS buffer solution for 5 minutes, the probe for labeling macrophages prepared in Example 2 (RITC-CGN, 0.5 mg/mL based on the carrageenan derivative) was treated for 20 minutes. Then, after washing twice with PBS for 3 minutes and pouring 100-200 μL of a PBS buffer solution, the well was observed with a fluorescence microscope.

3) Experimental Result

Figure 10:
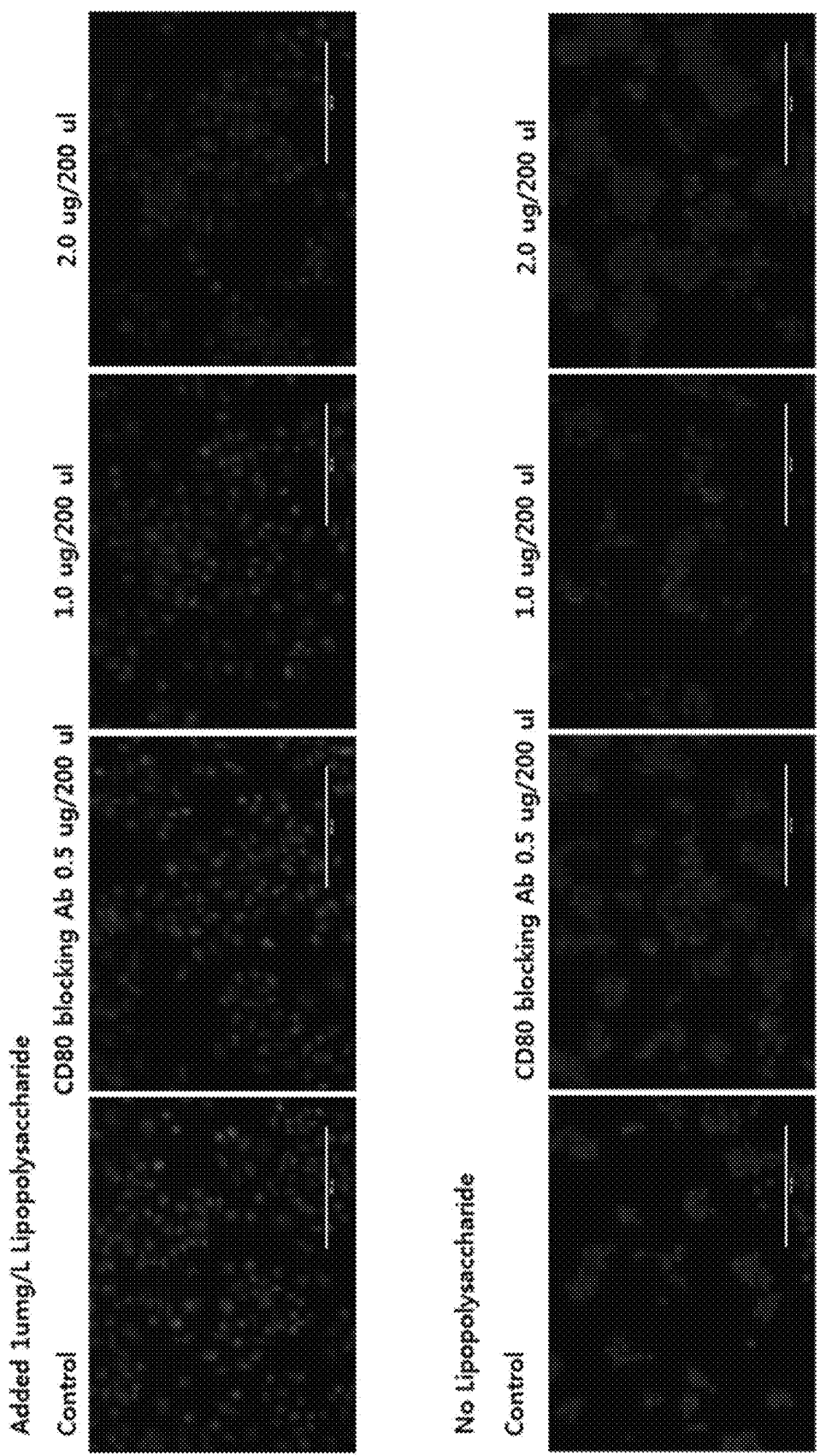
FIG. 10 shows the fluorescence microscopic images of test groups and a negative control group with treated CD80 antibody.
Figure 11:
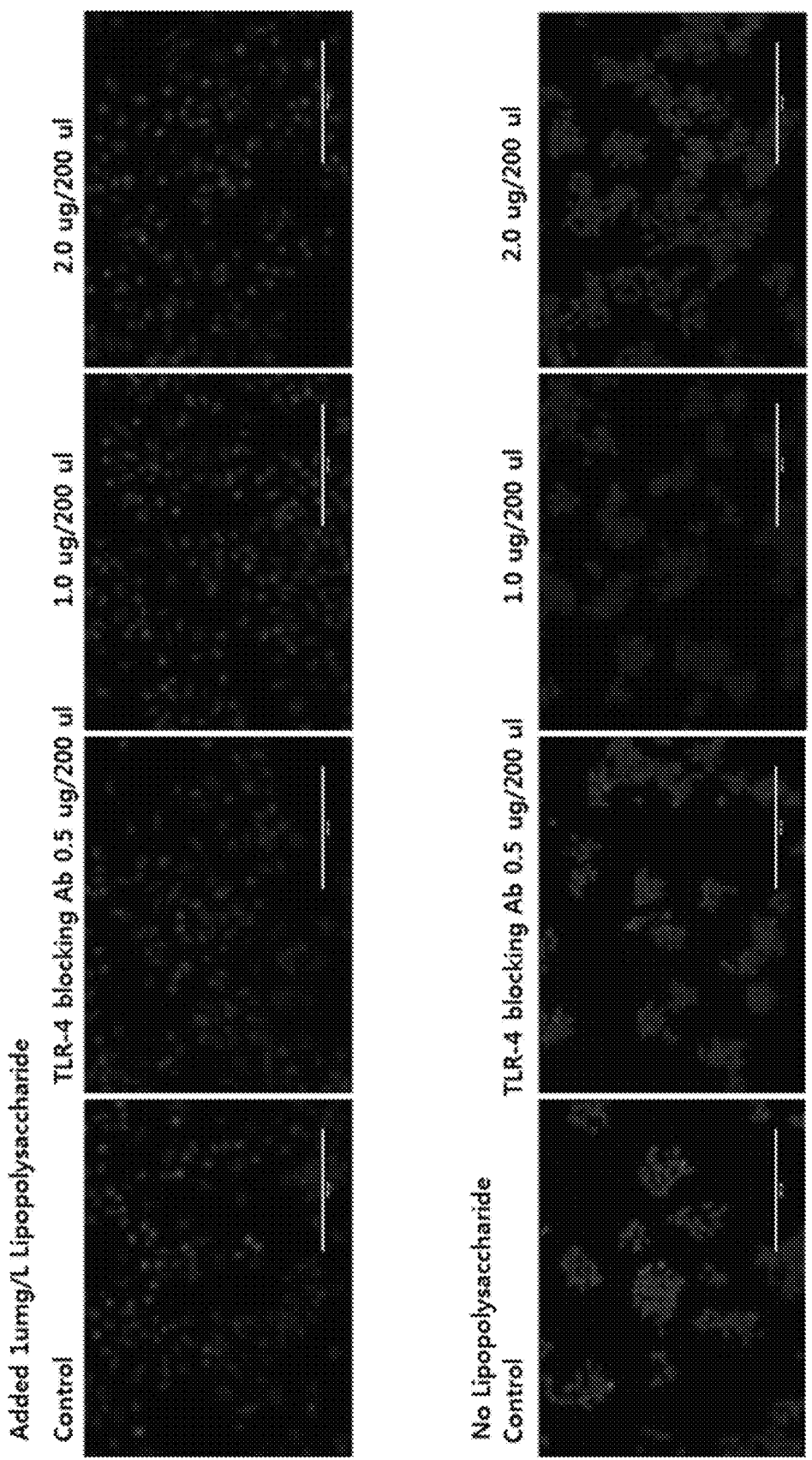
FIG. 11 shows the fluorescence microscopic images of test groups and a negative control group treated with TPR4 antibody.
Figure 12:
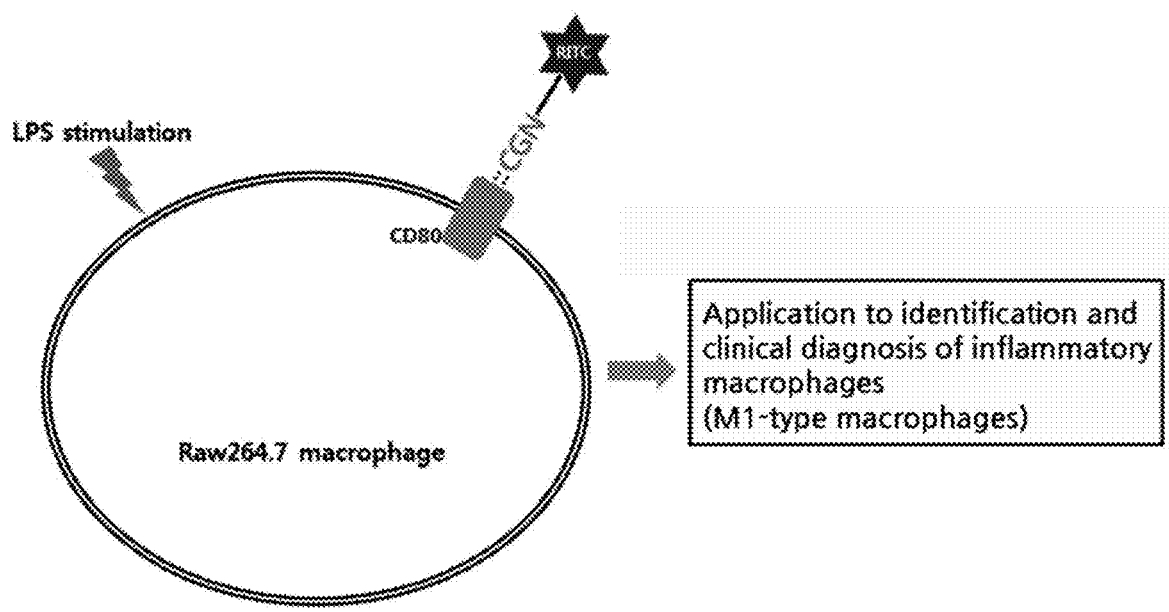
FIG. 12 shows mechanism of action of an RITC-labeled probe for labeling macrophages according to the present disclosure.

FIG. 10 shows the fluorescence microscopic images of the test groups and the negative control group treated with CD80 antibody, and FIG. 11 shows the fluorescence microscopic images of the test groups and the negative control group treated with TPR4 antibody.

As shown in FIGS. 10 and 11, in an in-vitro experiment, after inducing differentiation of macrophages into M1-type macrophages by treating with LPS (lipopolysaccharides), the M1 macrophages were treated with the receptor-specific CD80 blocking antibody and then the probe for labeling macrophages prepared in Example 2 (CGN-RITC) was added. As a result, as the CD80 present on the surface of the M1-type macrophages was blocked, the quantity (brightness) of the cells labeled with the probe for labeling macrophages prepared in Example 2 (CGN-RITC) was decreased gradually. In contrast, when TLR4 present on the surface of the M1-type macrophages was blocked, there was no change in the quantity of labeled cells. Through this, it can be seen that the probe for labeling macrophages according to the present disclosure (Example 2) binds specifically to CD80 of M1 macrophages.

Test Example 6. Analysis of Targeting Activity of Probe for Labeling Macrophages Prepared in Example 2 for M1 Macrophages (M1-Polarized THP-1 Cells)

1) Preparation of M1-Polarized THP-1 Cells

First, the differentiation of THP-1 cells was induced. Specifically, THP-1 cells were dispensed onto a 12-well plate, with 500,000 cells per well. Then, after treating each well with a PMA (phorbol 12-myristate 13-acetate) solution (final concentration: 100 ng/mL), the cells were cultured for 72 hours. The PMA solution was prepared by mixing in an RPMI medium containing 10% FBS and 1% antibiotic-antifungal solution, and a final volume of 1,000 μL was added. The PMA acts as a substance which induces differentiation of THP-1 cells from monocytes to macrophages.

Subsequently, the polarization of M1 macrophages into M1-polarized THP-1 cells was induced. Specifically, after completely removing the culture medium containing the differentiated THP-1 cells from each well, the well was washed once with a PBS buffer solution. Then, after treating each well with lipopolysaccharides (LPS) (final concentration: 1,000 ng/mL) and interferon-gamma (IFNγ) (final concentration: 20 ng/mL), the cells were cultured for 24 hours. The LPS and IFNγ were administered with a final volume of 1,000 μL after mixing in an RPMI 1640 medium supplemented with 10% FBS and 1% antibiotic-antifungal solution.

Then, M1-polarized THP-1 cells were prepared. Specifically, only the M1-polarized THP-1 cells were collected from the culture medium containing the M1-polarized THP-1 cells and then transferred to a 1.7-mL tube. The tube was centrifuged at 12,000 rpm for 1 minute and only the supernatant excluding pellets was removed. After washing the cells by adding 1 mL of a PBS buffer solution to the tube containing the remaining pellets, M1-polarized THP-1 cells (in pellet form) were separated from the supernatant by centrifugation and only the M1-polarized THP-1 cells were recovered by removing the supernatant.

2) Experiment

In order to investigate whether the RITC-labeled probe for labeling macrophages of the present disclosure acts specifically on M1-type macrophages, the recovered M1-polarized THP-1 cells were observed by flow cytometry after adding each sample.

A group treated with nothing (un-staining) was prepare as a control group, and a CD197-staining treated with 20 μL/mL M1 macrophage-targeting antibody FITC-CD197 was prepared as a comparison group. A CGN-staining group treated with the RITC-labeled probe for labeling macrophages prepared in Example 2 (RITC-CGN) at 0.5 mg/mL was prepared as a first test group, and a CD197+CGN-staining group treated with both RITC-CGN (Example 2) and FTIC-CD197 was prepared as a second test group. After adding each sample and conducting reaction at 4° C. for 30 minutes, 500 μL of a PBS buffer solution was added and the result was observed by flow cytometry.

3) Experimental Result

Figure 13:
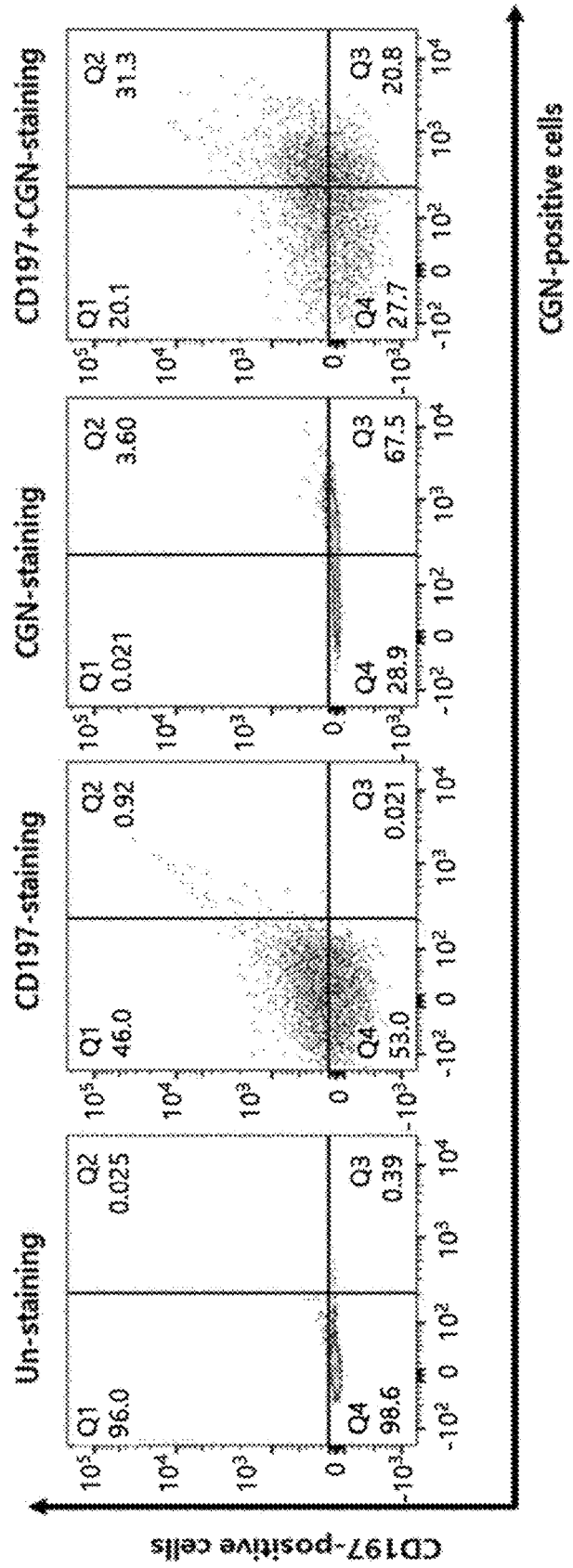
FIG. 13 shows a result of confirming that RITC-CGN reacts specifically with M1-type macrophages (differentiated THP-1 macrophages) by observing cellular distribution of by flow cytometry after staining with a probe for labeling macrophages prepared in Example 2 (RITC-CGN) or FITC-labeled CD197 (M1 differentiation marker).

FIG. 13 shows the result of preparing each group by adding M1 macrophage-targeting antibody FITC-CD197, the RITC-labeled probe for labeling macrophages prepared in Example 2 (RITC-CGN) or a mixture thereof to M1-polarized THP-1 cells and analyzing by flow cytometry.

The characteristics of M1 macrophages can be identified from the un-staining group as shown in FIG. 13. The cellular distribution of the comparison group, the first test group and the second test group was compared with respect to the cellular distribution of the un-staining group.

The cellular distribution of the comparison group (CD197-staining) shifted toward Q1 and Q2 (un-staining: 0.985%, CD197-staining: 46.92%). And, the cellular distribution of the first test group (CGN-staining) was observed to shift toward Q2 and Q3 (un-staining: 0.415%, CGN-staining: 71.1%).

It was observed that the cellular distribution of the second test group (CD197+CGN-staining), wherein the M1 macrophage-targeting antibody FITC-CD197 was mixed with the probe for labeling M1 macrophages prepared in Example 2 (RITC-CGN), shifted toward Q2 (CD197+CGN-staining: 31.3%).

Through this experiment, it was confirmed that the probe for labeling M1 macrophages prepared in Example 2 (RITC-CGN) reacts specifically with M1 macrophages.

We claim:

1. A carrageenan derivative formed as a hydroxy group of a galactose or 3,6-anhydrogalactose moiety of carrageenan having a repeat unit represented by Chemical Formula 1 is oxidized to an aldehyde group through periodate oxidation, and the aldehyde group is substituted with a compound represented by Chemical Formula 2 or Chemical Formula 3 and then reduced:

[Chemical Formula 1]

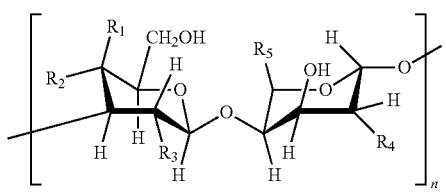

[Chemical Formula 2]

-continued

[Chemical Formula 3]

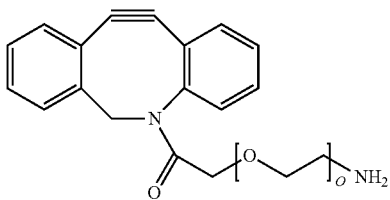

[Chemical Formula 1]

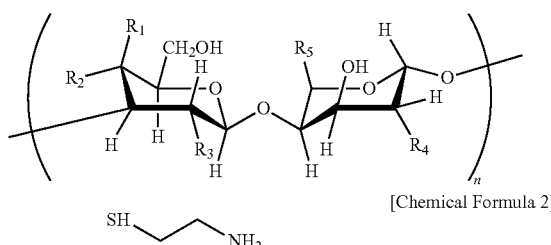

[Chemical Formula 2]

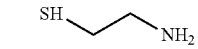

[Chemical Formula 3]

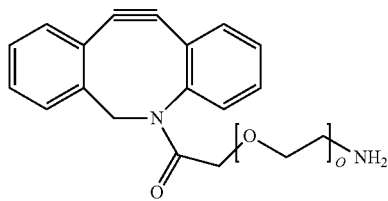

[Chemical Formula 4]

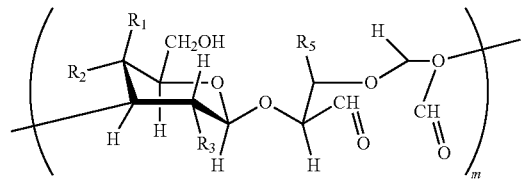

wherein each of $R_1$ to $R_4$, which are identical to or different from each other, is any one selected from the group consisting of —H, —OH, —$CH_3$, —$CH_2OH$, —COOH, and —$OSO_3^-$, $R_5$ is any one selected from the group consisting of —H, —OH, —$CH_3$, —$CH_2OH$, —COOH, —$CH_2OSO_3^-$, and —$OSO_3^-$, n is an integer from 1 to 10,000, and o is an integer from 1 to 10.

2. The carrageenan derivative according to claim 1, wherein the carrageenan represented by Chemical Formula 1 is represented by Chemical Formula c:

[Chemical Formula c]

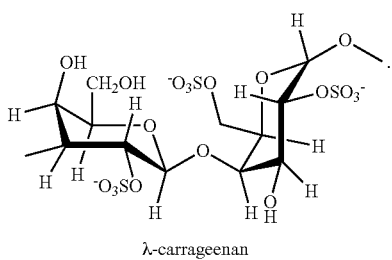

λ-carrageenan

3. The carrageenan derivative according to claim 1, wherein the carrageenan derivative acts as a ligand of CD80 of macrophages.

4. The carrageenan derivative according to claim 3, wherein the macrophages are M1-type macrophages.

5. A method for preparing a carrageenan derivative, comprising:

1) a step of preparing carrageenan-aldehyde having repeat units represented by Chemical Formulas 1 and 4 by reacting carrageenan having a repeat unit represented by Chemical Formula 1 with an oxidizing agent;

2) a step of substituting the aldehyde group of the carrageenan-aldehyde with a compound of Chemical Formula 2 or Chemical Formula 3 by reacting the carrageenan-aldehyde prepared in the step 1) with a compound represented by Chemical Formula 2 or Chemical Formula 3; and 3) a step of reacting the substituted carrageenan derivative prepared in the step 2) with a reducing agent:

wherein each of $R_1$ to $R_4$, which are identical to or different from each other, is any one selected from the group consisting of —H, —OH, —$CH_3$, —$CH_2OH$, —COOH, and —$OSO_3^-$, $R_5$ is any one selected from the group consisting of —H, —OH, —$CH_3$, —$CH_2OH$, —COOH, —$CH_2OSO_3^-$, and —$OSO_3^-$, each of n and m is an integer from 1 to 10,000, and o is an integer from 1 to 10.

6. The method for preparing a carrageenan derivative according to claim 5, wherein the oxidizing agent is sodium periodate.

7. The method for preparing a carrageenan derivative according to claim 5, wherein the oxidizing agent is added with an amount of 1-10 molar equivalents per unit of the carrageenan having a repeat unit represented by Chemical Formula 1.

8. The method for preparing a carrageenan derivative according to claim 5, wherein the step 1) is performed at 10-30° C. for 1-180 minutes.

9. The method for preparing a carrageenan derivative according to claim 5, wherein, in the step 2), the reaction is carried out such that 1-10 molecules of the compound represented by Chemical Formula 2 or Chemical Formula 3 is reacted per molecule of the carrageenan-aldehyde.

10. The method for preparing a carrageenan derivative according to claim 5, wherein the reducing agent is sodium cyanoborohydride ($NaCNBH_3$) or sodium borohydride.

11. A probe for labeling macrophages wherein a fluorescent dye or a radioisotope and the carrageenan derivative according to claim 1 are bound.

12. The probe for labeling macrophages according to claim 11, wherein the fluorescent dye is one or more selected from a group consisting of Cy3, Cy5, fluorescein isothiocyanate (FITC), SCN-RITC, tetramethylrhodamine isothiocyanate (RITC), Alexa, 4,4,-difluoro-4-bora-3a,4a-diaza-s-indacene (BODIPY), Texas Red, NOTA and biotin.

13. The probe for labeling macrophages according to claim 11, wherein the radioisotope is one or more selected from a group consisting of C-11, F-18, Ga-67, Ga-68, Cu-64, I-123, I-124, I-125, Zr-89, In-111, Tc-99m, Y-90, Re-186, Re-188, Lu-177, Ac-225, At-211 and I-131.

14. The probe for labeling macrophages according to claim 11, wherein the macrophages are derived by an inflammation-inducing factor.

15. The probe for labeling macrophages according to claim 11, wherein the probe for labeling macrophages specifically labels M1-type macrophages.

16. A method for preparing a probe for labeling macrophages, comprising:
   a) a step of preparing carrageenan-aldehyde having repeat units represented by Chemical Formulas 1 and 4 by reacting carrageenan having a repeat unit represented by Chemical Formula 1 with an oxidizing agent;
   b) a step of substituting an aldehyde group of the carrageenan-aldehyde with a compound of Chemical Formula 2 by reacting the carrageenan-aldehyde prepared in the step a) with a compound represented by Chemical Formula 2 or Chemical Formula 3;
   c) a step of reacting the substituted carrageenan derivative prepared in the step b) with a reducing agent; and
   d) a step of reacting the carrageenan derivative prepared in the step c) with a radioisotope or an isothiocyanate-modified fluorescent dye:

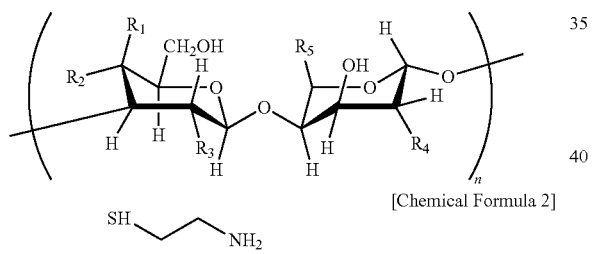

wherein
each of $R_1$ to $R_4$, which are identical to or different from each other, is any one selected from the group consisting of —H, —OH, —CH$_3$, —CH$_2$OH, —COOH, and —OSO$_3^-$, $R_5$ is any one selected from the group consisting of —H, —OH, —CH$_3$, —CH$_2$OH, —COOH, —CH$_2$OSO$_3^-$, and —OSO$_3^-$, each of n and m is an integer from 1 to 10,000, and o is an integer from 1 to 10.

17. A method for preparing a probe for labeling macrophages, comprising:
   i) a step of preparing carrageenan-aldehyde having repeat units represented by Chemical Formulas 1 and 4 by reacting carrageenan having a repeat unit represented by Chemical Formula 1 with an oxidizing agent;
   ii) a step of substituting an aldehyde group of the carrageenan-aldehyde with a compound of Chemical Formula 3 by reacting the carrageenan-aldehyde prepared in the step i) with a compound represented by Chemical Formula 2 or Chemical Formula 3;
   iii) a step of reacting the substituted carrageenan derivative prepared in the step ii) with a reducing agent; and
   iv) a step of conducting copper-free click reaction of the carrageenan derivative prepared in the step iii) with an azide compound represented by Chemical Formula 5:

wherein
each of $R_1$ to $R_4$, which are identical to or different from each other, is any one selected from the group consisting of —H, —OH, —CH$_3$, —CH$_2$OH, —COOH, and —OSO$_3^-$, $R_5$ is any one selected from the group consisting of —H, —OH, —CH$_3$, —CH$_2$OH, —COOH, —CH$_2$OSO$_3^-$, and —OSO$_3^-$, each of n and m is an integer from 1 to 10,000, and o is an integer from 1 to 10;

[Chemical Formula 5]

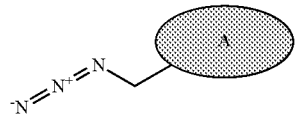

wherein

A is any one selected from a group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), Texas Red, NOTA, biotin, C-11, F-18, Ga-67, Ga-68, Cu-64, I-123, I-124, I-125, Zr-89, In-111, Tc-99m, Y-90, Re-186, Re-188, Lu-177, Ac-225, At-211 and I-131.

* * * * *